United States Patent
Posse

(10) Patent No.: US 11,221,388 B1
(45) Date of Patent: Jan. 11, 2022

(54) COMPENSATION OF MAGNETIC FIELD INHOMOGENEITY IN MR SPECTROSCOPIC IMAGING USING DYNAMIC K-SPACE EXPANSION IN COMBINATION WITH PARALLEL IMAGING

(71) Applicant: STC.UNM, Albuquerque, NM (US)

(72) Inventor: Stefan Posse, Albuquerque, NM (US)

(73) Assignee: UNM Rainforest Innovations, Albuquerque, NM (US)

( * ) Notice: Subject to any disclaimer, the term of this patent is extended or adjusted under 35 U.S.C. 154(b) by 1 day.

(21) Appl. No.: 16/442,358

(22) Filed: Jun. 14, 2019

Related U.S. Application Data

(60) Provisional application No. 62/685,746, filed on Jun. 15, 2018.

(51) Int. Cl.
    *G01R 33/565* (2006.01)
    *A61B 5/055* (2006.01)
    *A61B 5/00* (2006.01)
    *G01R 33/48* (2006.01)

(52) U.S. Cl.
    CPC ...... *G01R 33/56572* (2013.01); *A61B 5/0042* (2013.01); *A61B 5/055* (2013.01); *G01R 33/4818* (2013.01)

(58) Field of Classification Search
    CPC .......... G01R 33/56572; G01R 33/4818; A61B 5/0042; A61B 5/055
    See application file for complete search history.

(56) References Cited

U.S. PATENT DOCUMENTS

| | | | | |
|---|---|---|---|---|
| 2007/0252597 A1* | 11/2007 | Posse | ............... | G01R 33/485 324/312 |
| 2010/0034447 A1* | 2/2010 | Geier | ............... | G01R 33/482 382/131 |
| 2012/0249137 A1* | 10/2012 | Witschey | ......... | G01R 33/3875 324/309 |

OTHER PUBLICATIONS

S. Li, B. J. Dardzinski, C. M. Collins, Q. X. Yang, and M. B. Smith, "Three-dimensional mapping of the static magnetic field inside the human head," Magn Reson Med, vol. 36, pp. 705-714, Nov. 1996.
C. M. Collins, B. Yang, Q. X. Yang, and M. B. Smith, "Numerical calculations of the static magnetic field in three-dimensional multi-tissue models of the human head," Magn Reson Imaging, vol. 20, pp. 413-424, Jun. 2002.
D. H. Kim, E. Adalsteinsson, G. H. Glover, and D. M. Spielman, "Regularized higher-order in vivo shimming," Magnetic Resonance in Medicine, vol. 48, pp. 715-722, Oct. 2002.
A. M. Blamire, D. L. Rothman, and T. Nixon, "Dynamic shim updating: a new approach towards optimized whole brain shimming," Magn Reson Med, vol. 36, pp. 159-165, Jul. 1996.
L. M. Klassen and R. S. Menon, "Robust automated shimming technique using arbitrary mapping acquisition parameters (RASTAMAP)," Magnetic Resonance in Medicine, vol. 51, pp. 881-887, May 2004.
E. Schneider and G. Glover, "Rapid Invivo Proton Shimming," Magnetic Resonance in Medicine, vol. 18, pp. 335-347, Apr. 1991.

(Continued)

*Primary Examiner* — Gregory H Curran
(74) *Attorney, Agent, or Firm* — Keith A. Vogt; Keith Vogt, Ltd.

(57) ABSTRACT

A method for the compensation of magnetic field inhomogeneity in magnetic resonance spectroscopic imaging comprising the steps of using dynamic k-space expansion in combination with parallel imaging.

12 Claims, 24 Drawing Sheets

(56) References Cited

OTHER PUBLICATIONS

K. M. Koch, L. I. Sacolick, T. W. Nixon, S. McIntyre, D. L. Rothman, and R. A. de Graaf, "Dynamically shimmed multivoxel 1H magnetic resonance spectroscopy and multislice magnetic resonance spectroscopic imaging of the human brain," Magn Reson Med, vol. 57, pp. 587-591, Mar. 2007.

J. P. Stockmann, T. Witzel, B. Keil, J. R. Polimeni, A. Mareyam, C. LaPierre, K. Setsompop, and L. L. Wald, "A 32-channel combined RF and B shim array for 3T brain imaging," Magn Reson Med, Feb. 17, 2015.

A. Ebel and A. A. Maudsley, "Improved spectral quality for 3D MR spectroscopic imaging using a high spatial resolution acquisition strategy," Magn Reson Imaging, vol. 21, pp. 113-120, 2003.

S. Posse, "Direct imaging of magnetic field gradients by group spin-echo selection," Magn Reson Med, vol. 25, pp. 12-29, May 1992.

S. Posse, R. Otazo, S. R. Dager, and J. Alger, "MR spectroscopic imaging: Principles and recent advances," J Magn Reson Imaging, Nov. 27, 2012.

S. Posse, R. Otazo, A. Caprihan, J. Bustillo, H. Chen, P. G. Henry, M. Marjanska, C. Gasparovic, C. Zuo, V. Magnotta, B. Mueller, P. Mullins, P. Renshaw, K. Ugurbil, K. O. Lim, and J. R. Alger, "Proton echo-planar spectroscopic imaging of J-coupled resonances in human brain at 3 and 4 Tesla," Magn Reson Med, vol. 58, pp. 236-244, Aug. 2007.

S. Posse, Z. Shen, V. Kiselev, and L. J. Kemna, "Single-shot T2* mapping with 3D compensation of local susceptibility gradients in multiple regions," NeuroImage, vol. 18, pp. 390-400, 2003.

A. Caprihan, Li, T., Posse, S., "Single-Shot Interleaved Gradient Compensation of Susceptibility Induced Spectral Line Broadening in Proton Spectroscopic Echo-Planar Imaging (PEPSI)," in Proc. Int. Soc. Magn. Reson. Med., Seattle, WA, 2006, p. 70.

B. Jiang, X. Jiang, N. Xiao, X. Zhang, L. Jiang, X. A. Mao, and M. Liu, "Gridding and fast Fourier transformation on non-uniformly sparse sampled multidimensional NMR data," J Magn Reson, vol. 204, pp. 165-168, May 2010.

D. Marion, "Fast acquisition of NMR spectra using Fourier transform of non-equispaced data," J Biomol NMR, vol. 32, pp. 141-150, Jun. 2005.

S. Posse, R. Otazo, S. Y. Tsai, A. E. Yoshimoto, and F. H. Lin, "Single-shot magnetic resonance spectroscopic imaging with partial parallel imaging," Magn Reson Med, vol. 61, pp. 541-547, Mar. 2009, 2827332.

M. A. Griswold, P. M. Jakob, R. M. Heidemann, M. Nittka, V. Jellus, J. Wang, B. Kiefer, and A. Haase, "Generalized autocalibrating partially parallel acquisitions (GRAPPA)," Magn Reson Med, vol. 47, pp. 1202-1210, Jun. 2002.

K. P. Pruessmann, M. Weiger, M. B. Scheidegger, and P. Boesiger, "SENSE: sensitivity encoding for fast MRI," Magnetic Resonance in Medicine, vol. 42, pp. 952-962, Nov. 1999.

M. Lustig, D. Donoho, and J. M. Pauly, "Sparse MRI: The application of compressed sensing for rapid MR imaging," Magn Reson Med, vol. 58, pp. 1182-1195, Dec. 2007.

F. H. Lin, S. Y. Tsai, R. Otazo, A. Caprihan, L. L. Wald, J. W. Belliveau, and S. Posse, "Sensitivity-encoded (SENSE) proton echo-planar spectroscopic imaging (PEPSI) in the human brain," Magn Reson Med, vol. 57, pp. 249-257, Feb. 2007.

R. Otazo, S. Y. Tsai, F. H. Lin, and S. Posse, "Accelerated short-TE 3D proton echo-planar spectroscopic imaging using 2D-SENSE with a 32-channel array coil," Magn Reson Med, vol. 58, pp. 1107-1116, Dec. 2007.

S. Y. Tsai, S. Posse, Y. R. Lin, C. W. Ko, R. Otazo, H. W. Chung, and F. H. Lin, "Fast mapping of the T2 relaxation time of cerebral metabolites using proton echo-planar spectroscopic imaging (PEPSI)," Magn Reson Med, vol. 57, pp. 859-865, May 2007.

R. Otazo, Sodickson, D., Yoshimoto, A., Posse, S., "Accelerated Proton Echo-Planar Spectroscopic Imaging Using Parallel Imaging and Compressed Sensing.," in International Society for Magnetic Resonance in Medicine (ISMRM), 2009, p. 331.

K. P. Pruessmann, M. Weiger, P. Bornert, and P. Boesiger, "Advances in sensitivity encoding with arbitrary k-space trajectories," Magnetic Resonance in Medicine, vol. 46, pp. 638-651, Oct. 2001.

* cited by examiner

RF-Signal Data

Y-Value: 4.8388e-012
Y-Diff: 0

ADC Signal Data

Y-Value: 0
Y-Diff: 0

X Gradient

Y-Value: 0
Y-Diff: 0

Y Gradient

Y-Value: 2.36255e-013
Y-Diff: 0

Z Gradient

Y-Value: 1.77636e-015
Y-Diff: 0

0.X-Gradientmoment

Y-Value: 100.154
Y-Diff: 0

0.Y-Gradientmoment

Y-Value: -98.353
Y-Diff: 0

0. Z Gradientmoment

Y-Value: -91.178
Y-Diff: 0

FIG. 7B

| |
|---|
| RF-Signal Data<br>Y-Value: 3.98543e-011<br>Y-Diff: 0 |
| ADC Signal Data<br>Y-Value: 0<br>Y-Diff: 0 |
| X Gradient<br>Y-Value: 0<br>Y-Diff: 0 |
| Y Gradient<br>Y-Value: 2.5917e-012<br>Y-Diff: 0 |
| Z Gradient<br>Y-Value: 1.77636e-015<br>Y-Diff: 0 |
| 0. X-Gradientmoment<br>Y-Value: 100.154<br>Y-Diff: 0 |
| 0. Y-Gradientmoment<br>Y-Value: -99.89<br>Y-Diff. 0 |
| 0. Z Gradientnmoment<br>Y-Value: -91.178<br>Y-Diff: 0 |

FIG. 8B

COMPENSATION OF MAGNETIC FIELD INHOMOGENEITY IN MR SPECTROSCOPIC IMAGING USING DYNAMIC K-SPACE EXPANSION IN COMBINATION WITH PARALLEL IMAGING

RELATED APPLICATIONS

This application claims priority to U.S. Provisional Application Ser. No. 62/685,746 filed on Jun. 15, 2018, which is incorporated herein in its entirety.

STATEMENT REGARDING FEDERALLY SPONSORED RESEARCH & DEVELOPMENT

Not Applicable.

INCORPORATION BY REFERENCE OF MATERIAL SUBMITTED ON A COMPACT DISC

Not applicable.

BACKGROUND OF THE INVENTION

Spectral line broadening due to inhomogeneity of the static magnetic field ($B_0$) remains as one of the most challenging problems in MR spectroscopic imaging (MRSI), severely limiting in vivo applications and hampering clinical acceptance. Spectral line broadening not only reduces detection sensitivity and impairs spectral quantification of overlapping resonances, but it also hampers spectral identification. As a consequence, it is very difficult to reliably measure singlet concentrations in the orbital frontal cortex and in the temporal lobe, and to almost impossible to measure multiple resonances in these brain regions. Frequency shifts between voxels due to magnetic field inhomogeneity, which can be as large as 6 parts-per-million (ppm) across the brain, decrease the effectiveness of water suppression and introduces spatial aliasing of poorly suppressed water signal into adjacent regions, resulting in distant baseline artifacts. Higher order auto-shimming (HOAS), provided on most high-field scanners, offers limited capability for correction of $B_0$ field inhomogeneity. Extending the capability of the existing field coil design requires either a larger number of higher order shim coils, or better control over the existing coils. To increase control, one study showed that a dynamic shim state, matching the current acquisition slice, can improve the corrective power of the shim coils by reducing the spatial constraints on the shim state. Subsequent studies have further demonstrated the effectiveness of this approach. Switched higher order shimming between different slabs has shown an advantage over increasing the numbers of shim coils, but these hardware-intensive solutions are not yet available on clinical scanners. Recently, the integration of multi-coil $B_0$ shimming into the design of RF array coils has improved $B_0$ shimming performance over standard second-order spherical harmonics shimming[8]. However, considerable magnetic field inhomogeneity remains in the orbital frontal cortex and in medial temporal lobes. It has been shown that reducing the voxel size in MRSI reduces the effect of B0 inhomogeneity and reduces spectral line broadening. However, this approach is very costly, as SNR per unit time decreases linearly with voxel volume.

Local magnetic field gradients due to $B_0$ inhomogeneity interfere with the spatial encoding by readout and phase encoding gradients and the resulting signal dephasing increases with increasing spectral encoding time. Mathematically, this effect can be described using the formalism of group spin-echo shift in k-space, which was developed for gradient echo imaging and is directly applicable to MRSI. The k-space points for the first spectral encoding time constitute a time slice within which the spatially encoded signal refocuses at the center of the slice at k=0. In the absence of local gradients, the center of k-space is invariant with respect to spectral encoding time. However, a local gradient $G_l$ causes refocusing of the spatially encoded signal from that region to be shifted within the time slice. This local k-space signal shift $\Delta k = -\gamma G_l t$ (which represents a shift of the k-space origin in that region) increases linearly with spectral encoding time t and results in a signal being lost once the boundaries of the encoded k-space (maximum k-space vectors ($k_{max}$)) are reached (FIG. 1). The shortened effective measurement time $t_{eff} = k_{max} * \gamma * G_l$ of the corresponding group spin echo from the vicinity of the local gradient $G_l$ results in spectral line broadening ($1/t_{eff}$) in that region. Local gradients within an imaging volume have different orientations and magnitudes, resulting in a progressive dispersion of the measured signals within the acquired k-t data space, as spectral encoding time t increases. Compensation of local gradients in Proton Echo Planar Spectroscopic Imaging (PEPSI) using shim gradient interleaved between readout gradients is a component of the present invention. Inspired by the development of interleaved shimming in multi-echo fMRI, in one embodiment, the present invention provides a dynamic shimming method that interleaves alternating positive and negative gradient blips between PEPSI readout gradients to counteract the dephasing caused by local gradients. The alternating gradients are balanced to refocus the signal periodically in brain regions not affected by the local gradient. This approach allows to compensate local gradients in a selected brain region and simultaneously acquire signals from the rest of the brain without compensation as shown FIGS. 2A and 2B. Specifically, FIG. 2B shows the special case where 2 distinct linear k-space trajectories are acquired to compensate two regions with different spatially uniform local gradients. This interleaved shimming approach corresponds to linearly expanding k-space for two specific local gradient vectors and is most effective in regions with uniform local gradient amplitudes and directions, which is to some extent the case in the amygdala. It is less effective in regions with nonlinear local gradients.

BRIEF SUMMARY OF THE INVENTION

In one embodiment, the present invention provides for the global compensation of spectral line broadening in multiple regions with differing local gradient vectors.

In another embodiment, the present invention provides for the global compensation of spectral line broadening in multiple regions with differing local gradient vectors by expanding k-space with increasing spectral encoding time t, using increasing readout gradients moments and interleaving of alternating positive and negative gradient blips with increasing gradient moments between echo-planar spatial-spectral readout gradients to counteract the dephasing caused by local gradients, resulting in spectral line narrowing in proportion to the expansion of k-space.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

In the drawings, which are not necessarily drawn to scale, like numerals may describe substantially similar components throughout the several views. Like numerals having different letter suffixes may represent different instances of substantially similar components. The drawings illustrate generally, by way of example, but not by way of limitation, a detailed description of certain embodiments discussed in the present document.

FIGS. 7A and 7B show a PEPSI pulse sequence simulation of excitation and readout modules with linear expansion of k-t-space encoding using 6 different readout gradient train segments. The simulation shows the first phase encoding step with maximum positive $k_y$ encoding moment (see Y Gradient and Y-Gradient moment).

FIGS. 8A and 8B show a corresponding simulation of the central phase encoding step with minimum $k_y$ encoding moment (see Y Gradient and Y-Gradient moment).

DETAILED DESCRIPTION OF THE INVENTION

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a representative basis for teaching one skilled in the art to variously employ the present invention in virtually any appropriately detailed method, structure, or system. Further, the terms and phrases used herein are not intended to be limiting, but rather to provide an understandable description of the invention.

Compensation of Local Gradients by Dynamic Case k-Space Expansion

In one embodiment, the present invention provides for the global compensation of spectral line broadening in multiple regions with differing local gradient vectors. This may be accomplished by expanding the k-space with increasing spectral encoding time t, resulting in spectral line narrowing in proportion to the expansion of k-space. This k-space expansion approach does not increase spatial encoding time and it is more SNR efficient than approaches that increase spatial resolution.

Increasing spatial resolution requires uniform expansion of k-space for all time slices, thus penalizing early time slices. However, expansion of k-space with spectral encoding time requires interleaving progressively stronger spatial encoding into the spectral acquisition and consequent elongation of the spectral dwell time, which decreases spectral bandwidth.

The resulting undersampling, which increases with spectral encoding time is feasible, however, since spectral information density in k-t-space is typically sparse and decreases with increasing spectral encoding time. Spectral reconstruction of nonuniformly sampled data is performed by applying either non-uniform fast Fourier transform (NUFFT) regridding or expanded Fourier Transform, a MATLAB toolbox (https://www.mathworks.com/matlabcentral/fileexchange/11020-extended-dft). For example, the proton spectrum is quite sparse at long time delays and contains only a few peaks (water, Ino, Cho, Cr, NAA and perhaps lipids and lactate), which facilitates this approach. Spectral reconstruction of nonlinearly sampled data is well established using the non-linear Fourier Transform.

Figure 1:
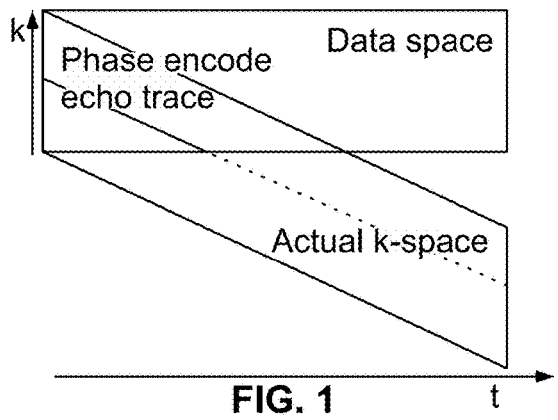
FIG. 1 shows an example of local group spin echo shifts in k-t-space where local gradients progressively move the signal maximum (phase encoding echo) outside of data space and a shorter data trace in the time domain corresponds to a filter and causes line broadening.
Figure 2B:
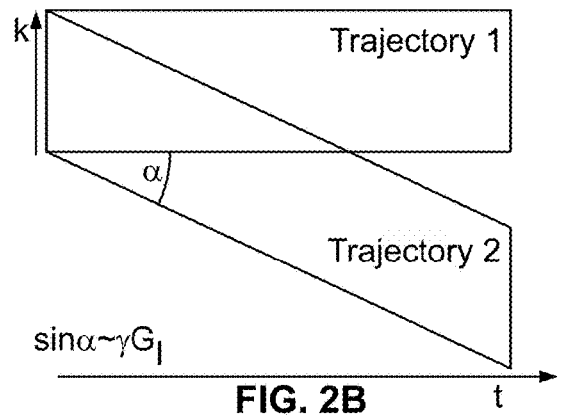
FIG. 2B depicts the two distinct linear k-space trajectories that are encoded using the interleaved shimming method described in FIG. 2A.
Figure 2A:
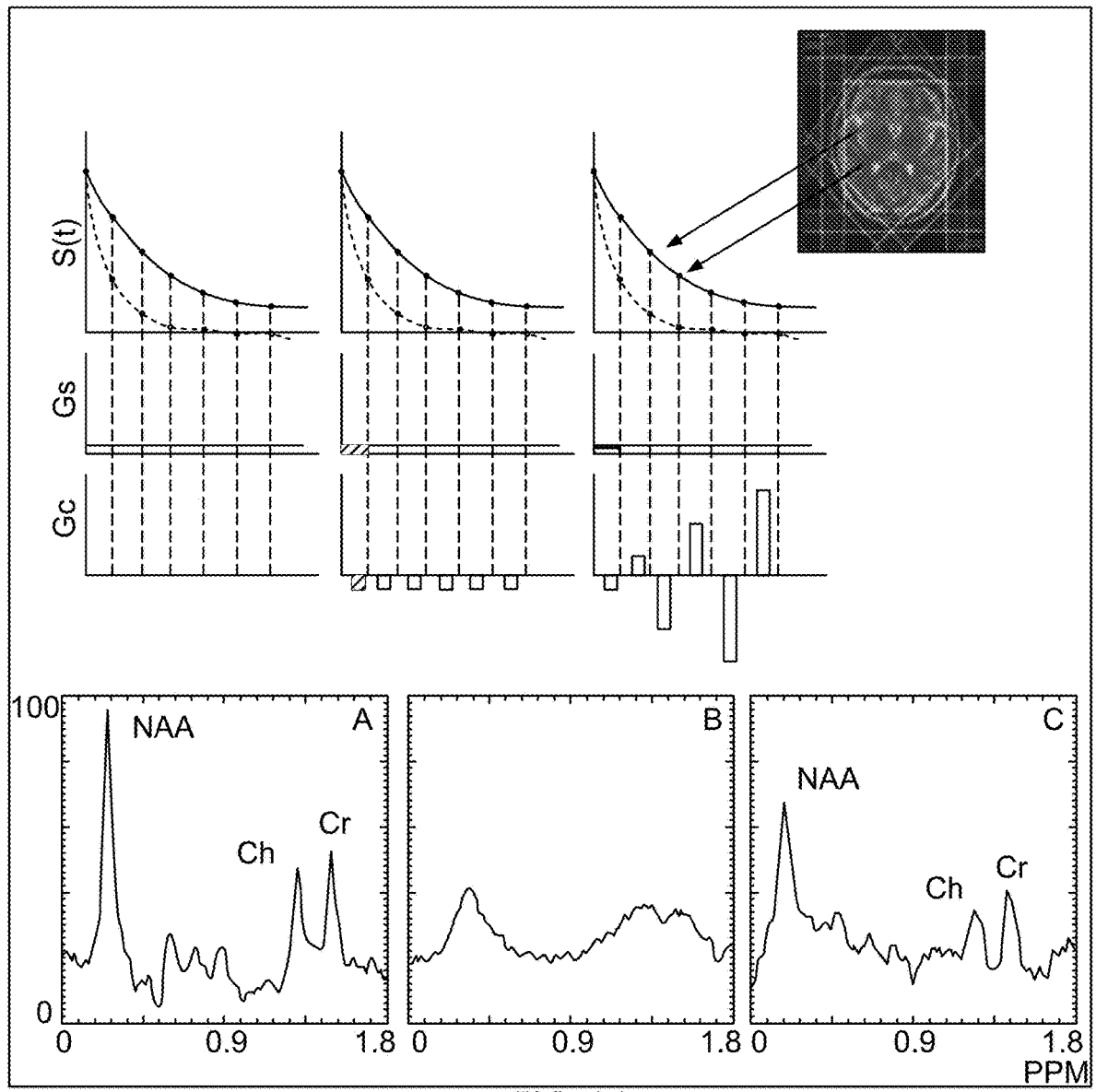
FIG. 2A shows a single-shot spectroscopic imaging method that compensates local gradients in regions that suffer from susceptibility related spectral line broadening.
Figure 3:
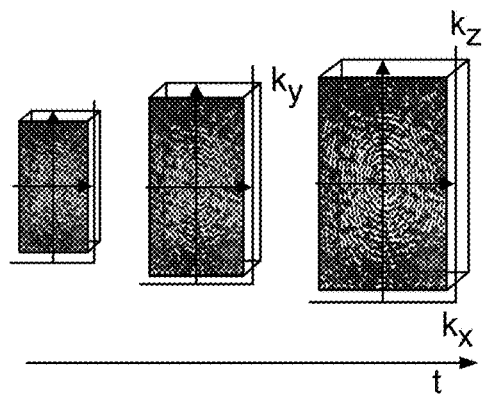
FIG. 3 shows an example of linear expansion of k-t-space encoding to capture the expansion of local group spin echo shifts along the k-t-space axes.

This k-space expansion approach is compatible with conventional phase encoded MRSI and particularly suitable for high-speed MRSI, such as echo-planar MRSI and spiral MRSI. With echo-planar encoding, increasing the readout gradient moment with spectral encoding time expands kz and interleaving blipped phase encoding gradients (e.g. using single-shot interleaved phase encoding) expands $k_y$ and $k_z$ as shown in FIG. 3. Specifically, FIG. 3 is a generalization, which compensates local gradients with arbitrary orientations and a range of amplitudes with a maximum amplitude that corresponds to the rate of change in k-space extent.

With spiral MRSI, expanding k-space can be accomplished by extending the spiral encoding module. More complex multi-axis gradient waveforms (e.g. to encode spherical trajectories) or combinations thereof, and switched nonlinear surface gradients, may also be particularly effective for dynamic k-space expansion. As gradient moments increase to encode the expanding k-space it becomes necessary to increase the spectral dwell time to accommodate the increasingly longer gradient encoding modules, leading to a decrease of the sampled spectral width, which must still fulfill the Nyquist criterion for sampling a minimum spectral width that fully resolves aliased spectral peaks.

A preferred implementation that minimizes gradient switching tailors the expansion and density of k-t-space sampling to the dispersion and density of signal trajectories in k-t-space, which can be directly predicted from $B_0$ mapping.

Combining Gradient Encoding with Partial Parallel Imaging and Compressed Sensing The expansion of k-space may necessitate progressive k-space undersampling to maintain a desired maximum spectral dwell time. To relax the requirements of gradient encoding, in another embodiment, the present invention undersamples k-space either regularly or randomly, and uses partial parallel imaging or compressed sensing to reconstruct the missing data. The combination of high-speed MRSI with partial parallel imaging using GRAPPA and SENSE, and compressed sensing, has been introduced. In other aspects, the present invention samples the initial time slices without undersampling to enable computation of the reconstruction k-space kernel in case of GRAPPA or the sensitivity profiles for image space unfolding in case of SENSE. In still further aspects, the present invention is configured to increasingly undersample k-space with increasing spectral encoding time to maintain a desired maximum spectral dwell time.

Figure 4A:
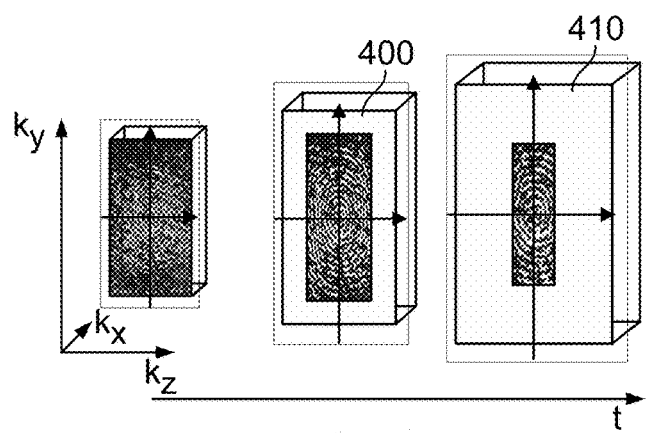
FIG. 4A provides an example of linear expansion of k-t-space encoding in 3 time slices for sections delineating k-t-space regions that are encoded using interleaved phase encoding.
Figure 4B:
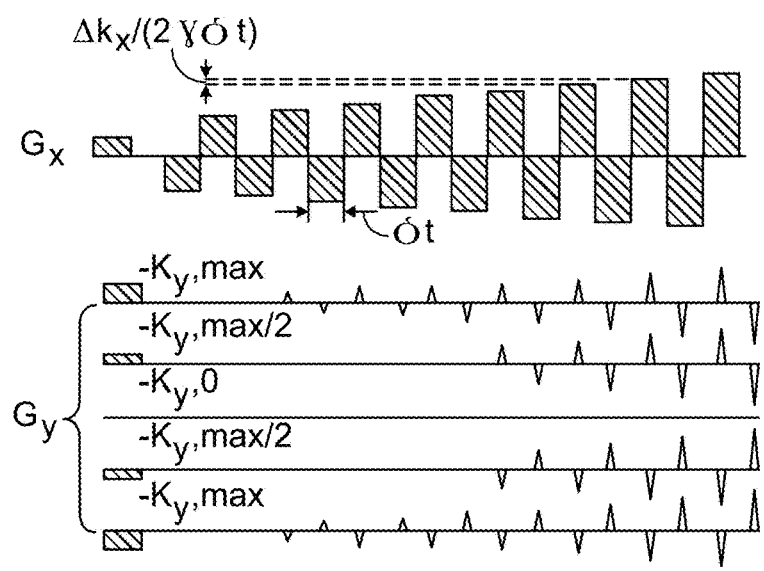
FIG. 4B provides an example of linear expansion of k-t-space encoding in 3 time slices for a 2D PEPSI readout module with 2×2-fold k-space expansion using a linear increase in readout gradient moment and interleaved phase encoding gradients blips as a function of conventional phase encoding step ($k_y$) and t.
Figure 4C:
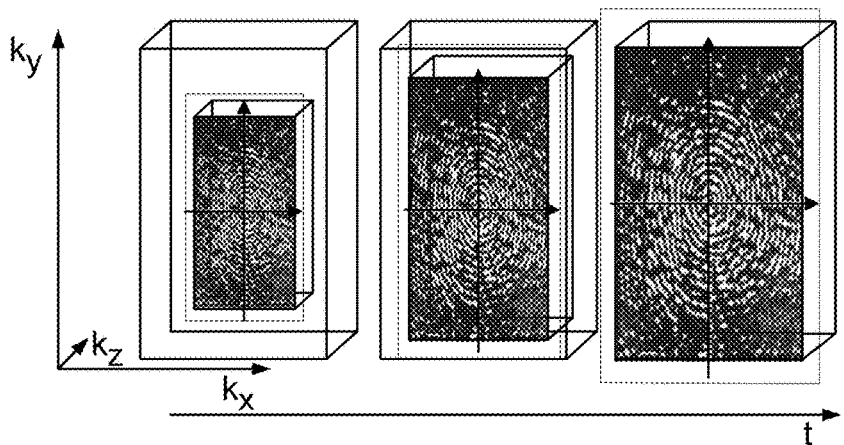
FIG. 4C shows zero filling of k-space depicted by empty sections of bounding boxes to obtain consistent data sizes across time slices.

Dynamic K-Space Expansion in PEPSI Using Increasing Readout Gradient and Interleaved Phase Encoding Gradient Moments In other aspects of the present invention, the linear expansion of k-t-space may use a readout gradient moment with stepwise increases ($2G_r\delta t$) every second gradient using a constant gradient duration $\delta$, up to the limits of the gradient performance. Single-shot phase encoding using gradient blips with linearly increasing gradient moment $G_l*t$ are selectively interleaved into the PEPSI readout, with a corresponding increase of the effective spectral dwell time. To minimize the SNR loss in magnetically homogeneous areas, the interleaving will start at the edges of the original $k_y$-$k_z$-space and progressively insert single-shot phase encoding into more central $k_y$-$k_z$-space encodings as time t increases, as shown in FIGS. 4A-4C. In FIG. 4A, sections 400 and 410 delineate k-t-space regions that are encoded using interleaved phase encoding.

The k-space dependent time delay $\Delta t$ of this insertion is $\Delta t = T(k_{max}-k)/k_{max}$, where T is the total readout duration and $k_{max}$ is the extent of the original k-space. To maximize SNR, the extent of k-t-space expansion along the different k-space dimensions is tailored to the orientation and amplitude distribution of local Gradients $G_l$ based on $B_0$ gradient maps. The SNR scales to at least with the square root of the decrease in voxel size in regions with magnetic field inhomogeneity depending on the histogram of local magnetic field gradients in the volume of interest. This k-t-space expansion method provides a reduction in line width that is comparable to that of increasing spatial resolution, however, with much improved SNR and without increase in scan time. A $\sqrt{2}$ larger gain in SNR may be obtained in magnetically homogeneous brain regions.

Reconstruction

Zero-filling of time-slice data in the k-space domain is performed as a first step to obtain consistent k-space matrix size across time slices as shown in FIG. 4C. Spectral reconstruction is performed by applying non-uniform fast Fourier transform (NUFFT) regridding or the expanded Fourier Transform MATLAB toolbox. Conventional Fourier-based spatial reconstruction is performed either before or after spectral reconstruction. This k-t-space expansion method is compatible with partial parallel imaging using SENSE and GRAPPA.

Figure 5A:
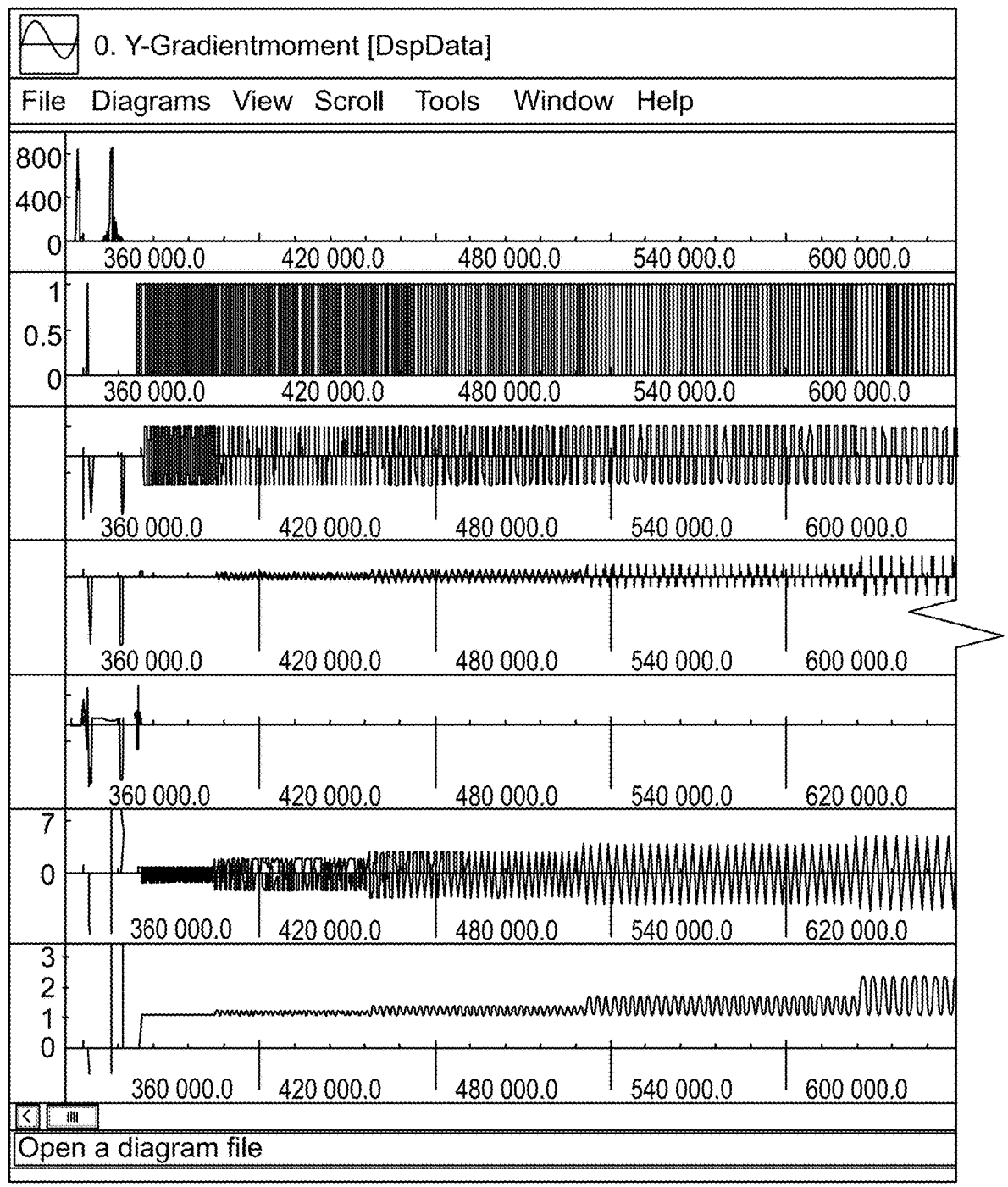
FIGS. 5A and 5B show a PEPSI pulse sequence simulation of excitation and readout modules with the linear expansion of k-t-space encoding using 6 different readout gradient train segments with increasing readout gradient and phase encoding gradient moments, and corresponding increases in ADC duration at constant dwell time.
Figure 5B:
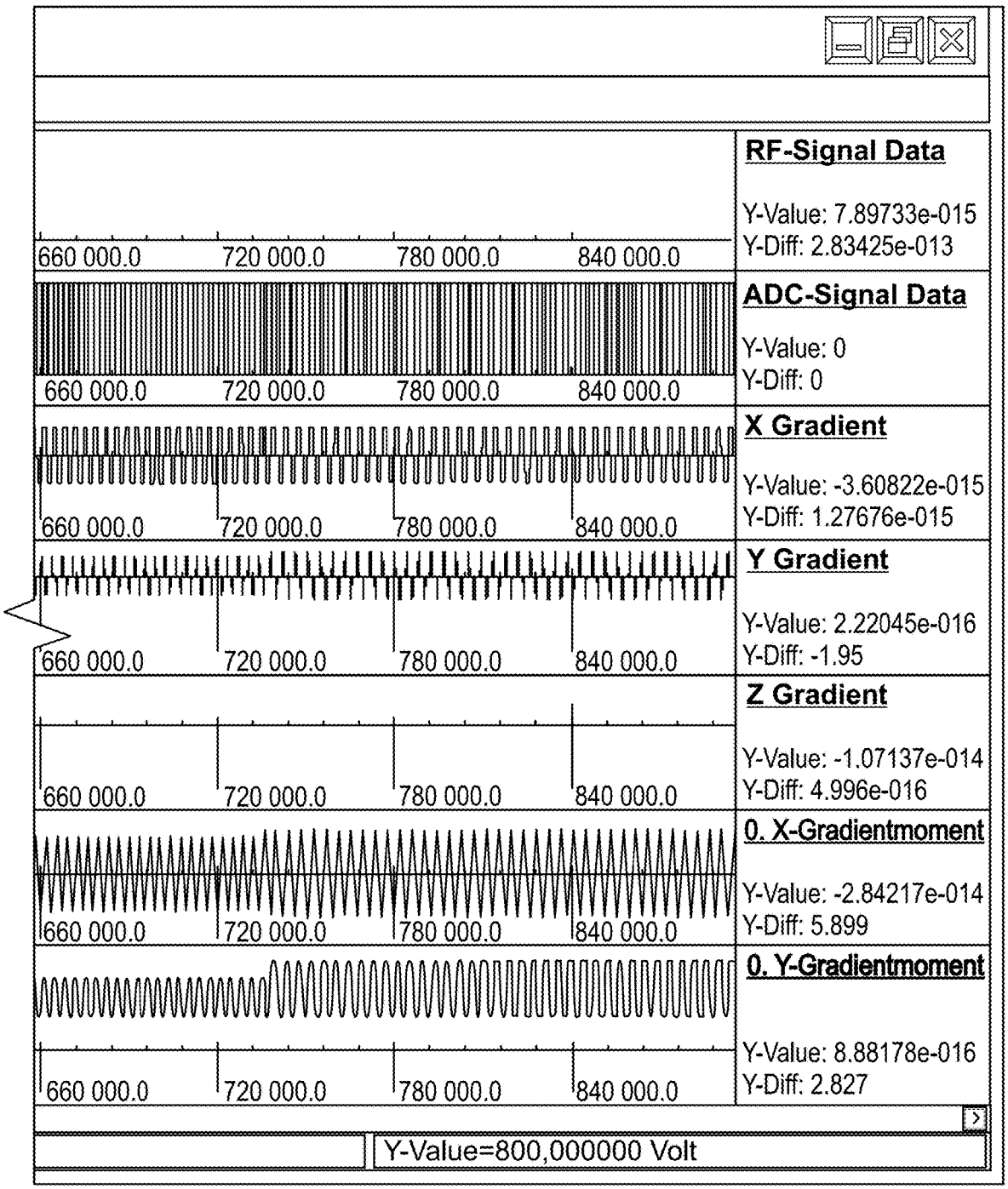
Figure 6A:
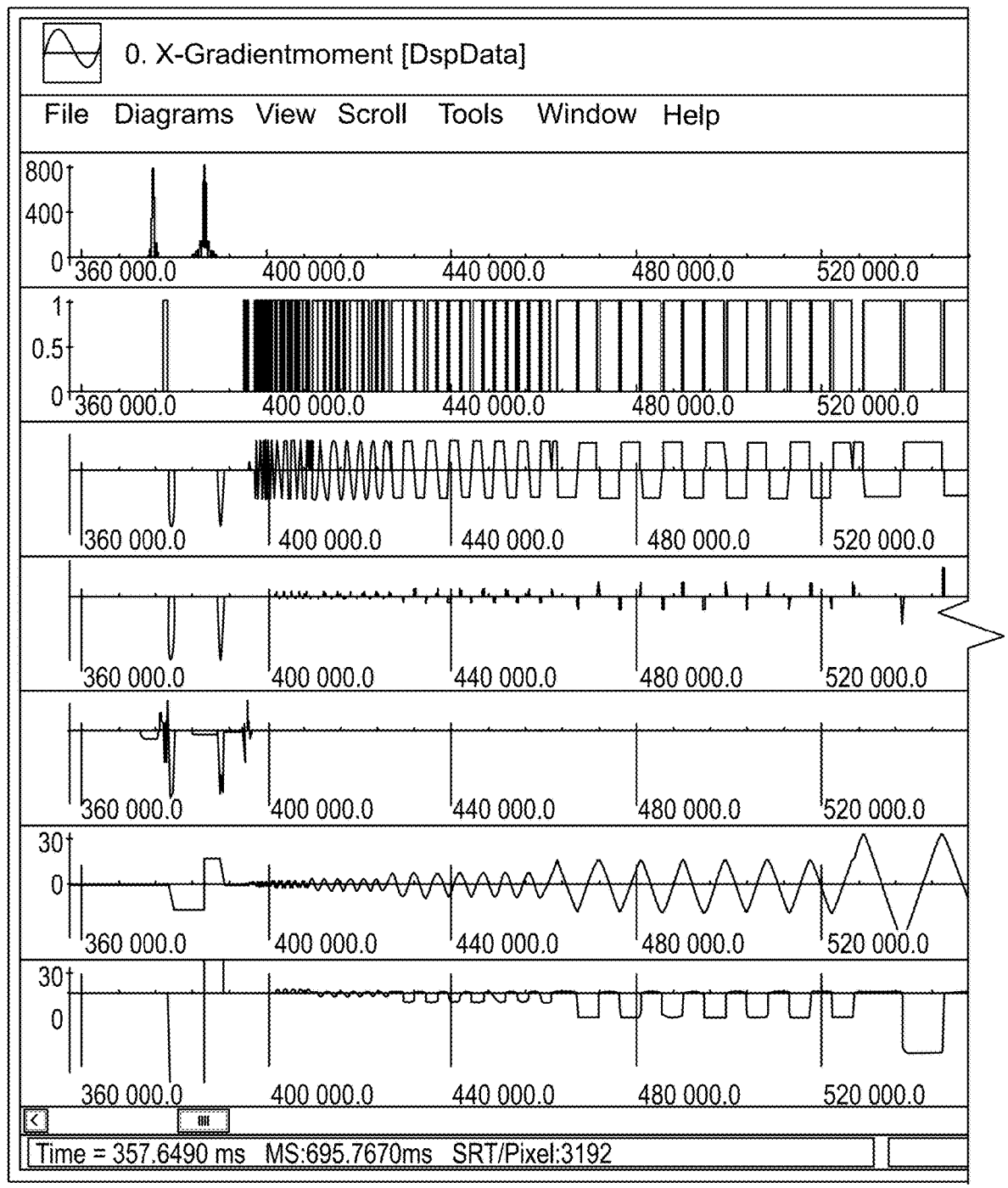
FIGS. 6A, 6B and 6C show a corresponding PEPSI pulse sequence simulation with the nonlinear expansion of k-t-space encoding using 6 different readout gradient train segments with nonlinearly increasing readout gradient and phase encoding gradient moments, and corresponding increases in ADC duration at constant dwell time.
Figure 6B:
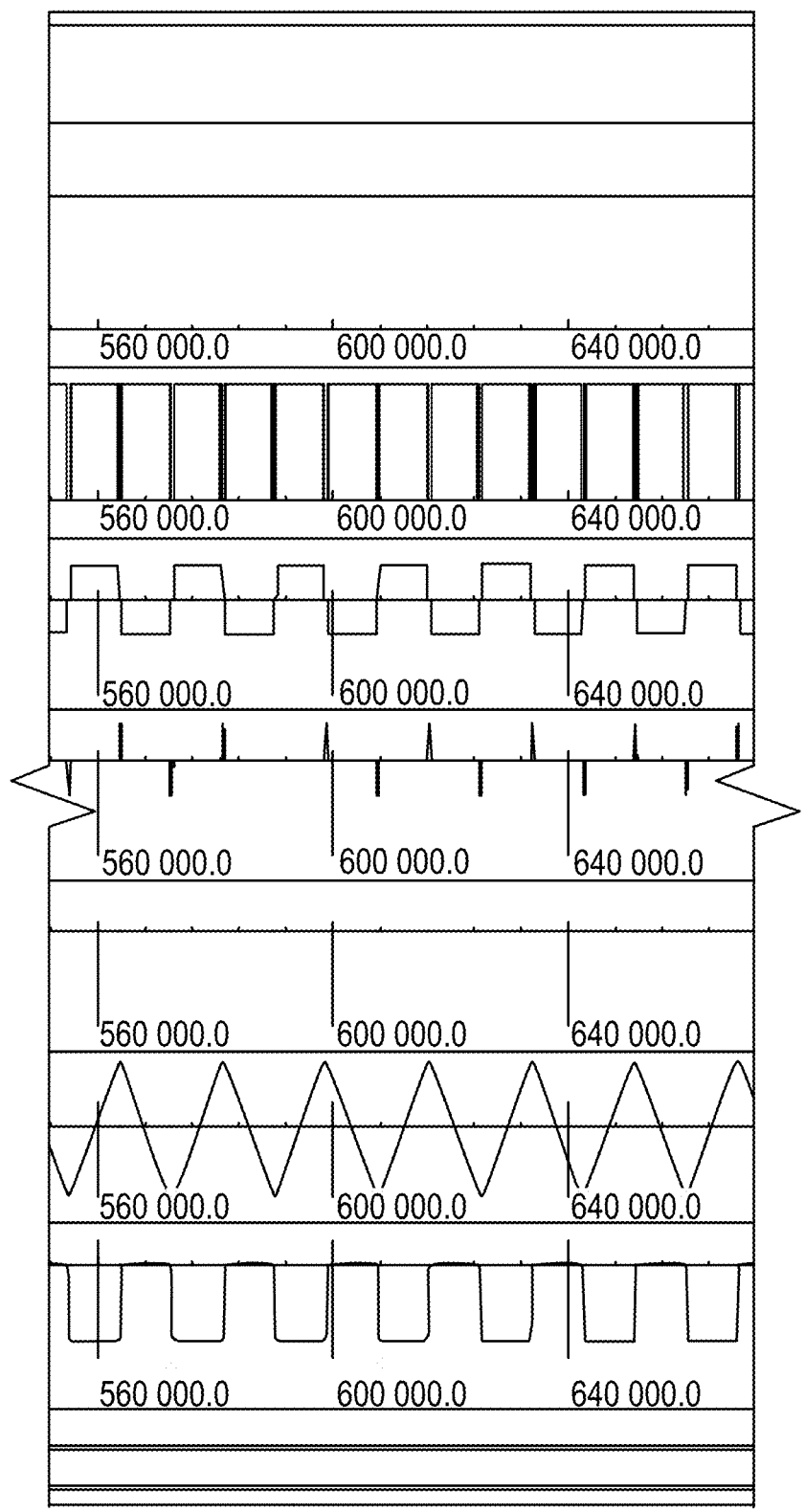
Figure 6C:
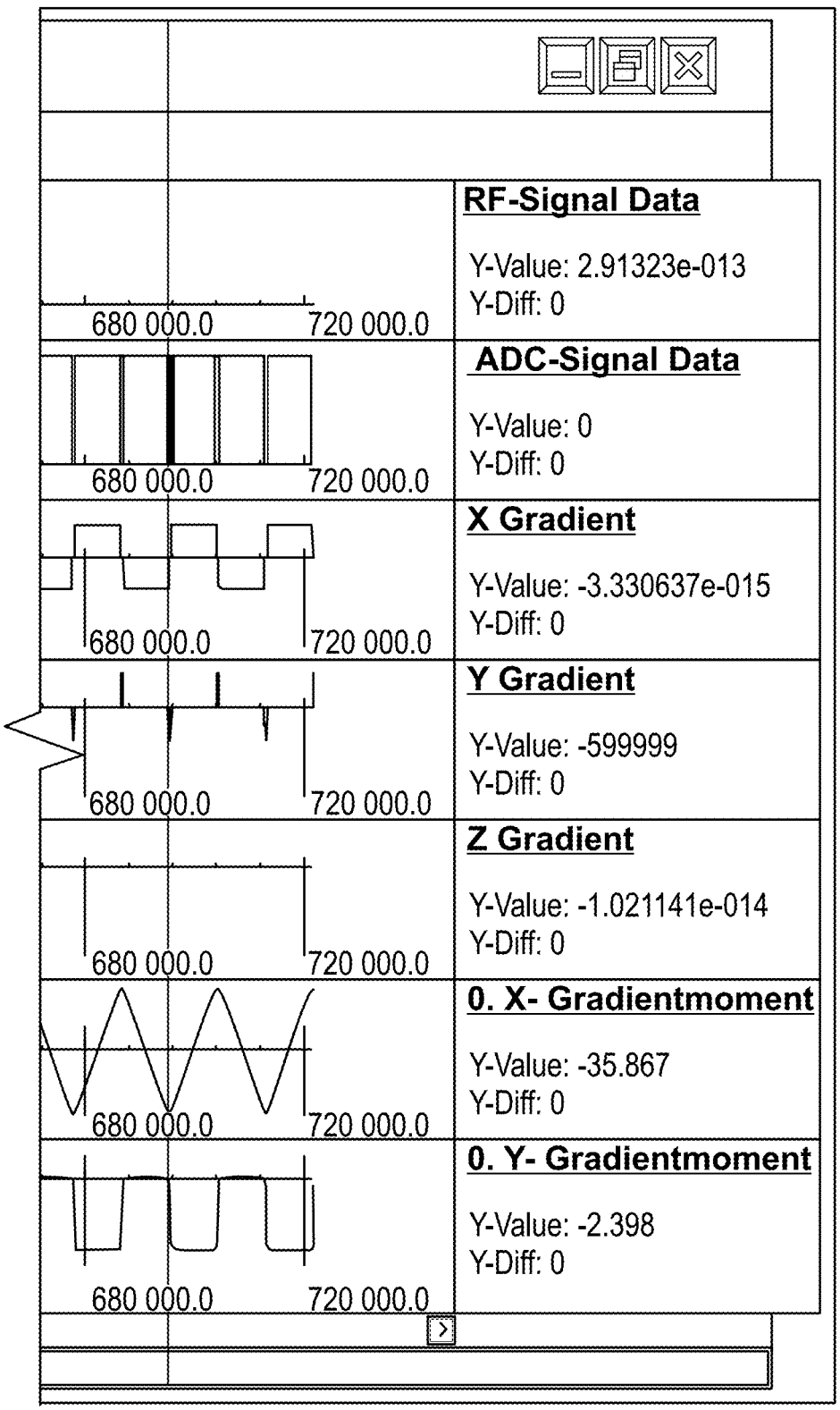
Figure 7A:
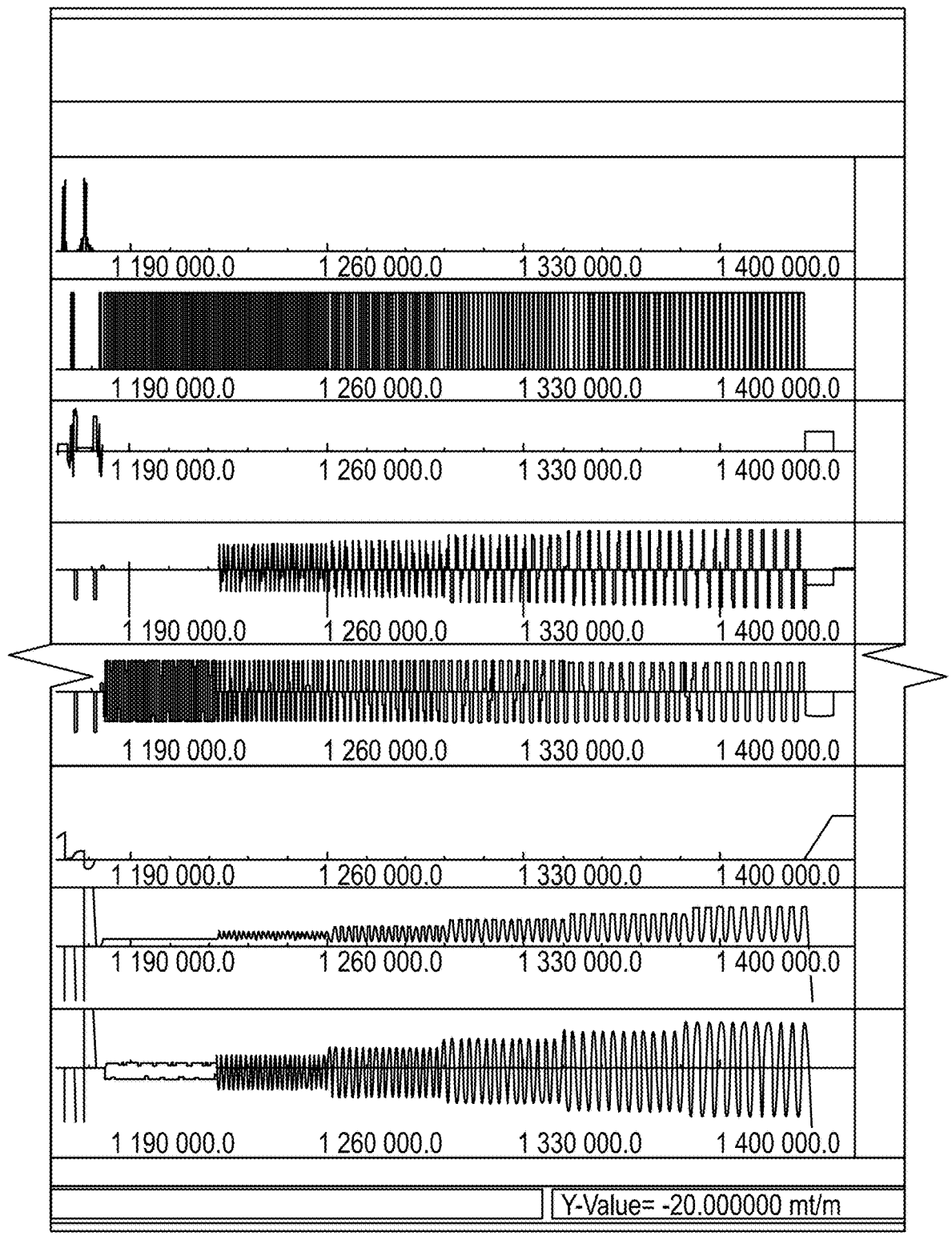
Figure 8A:
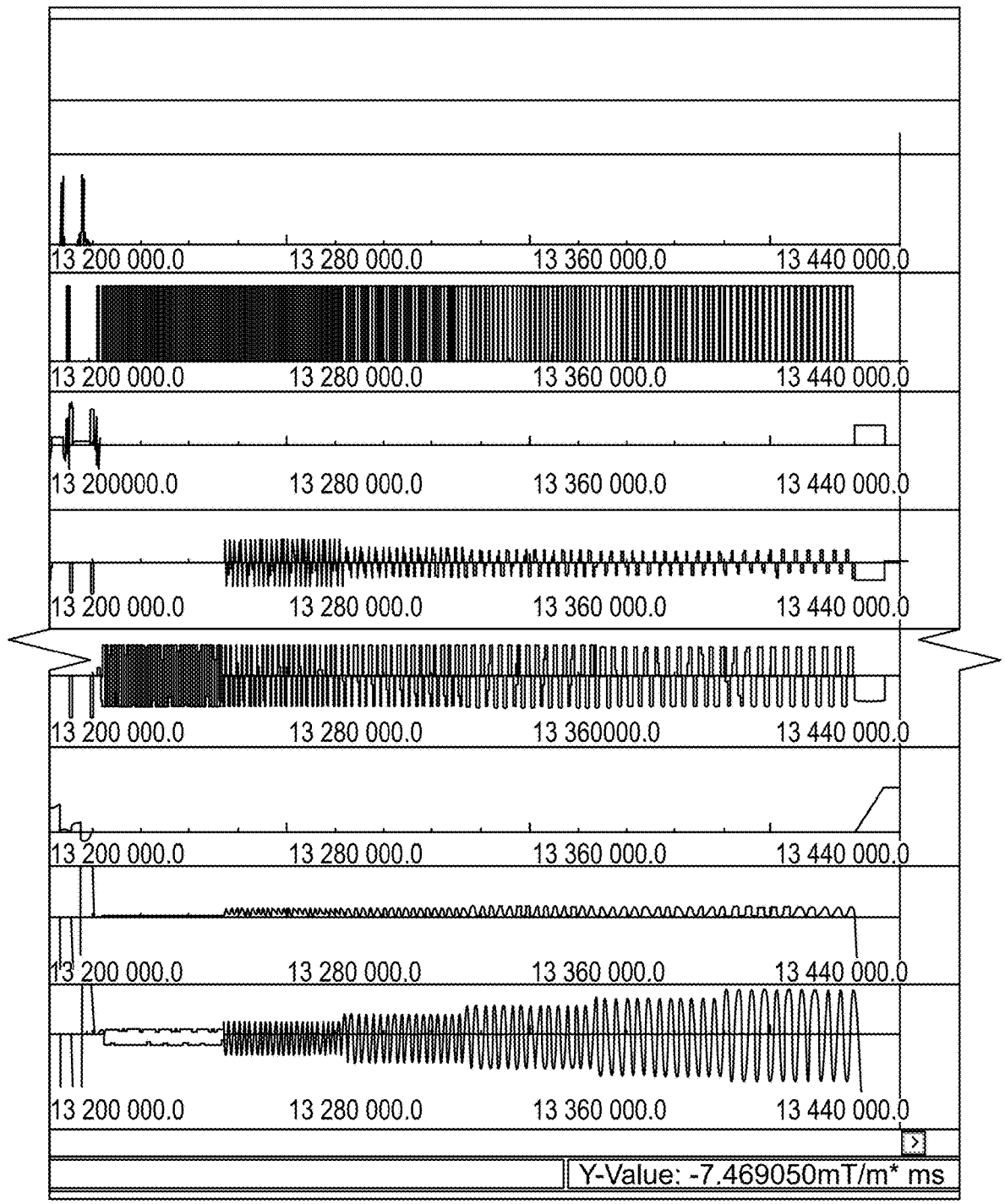
Figure 9A:
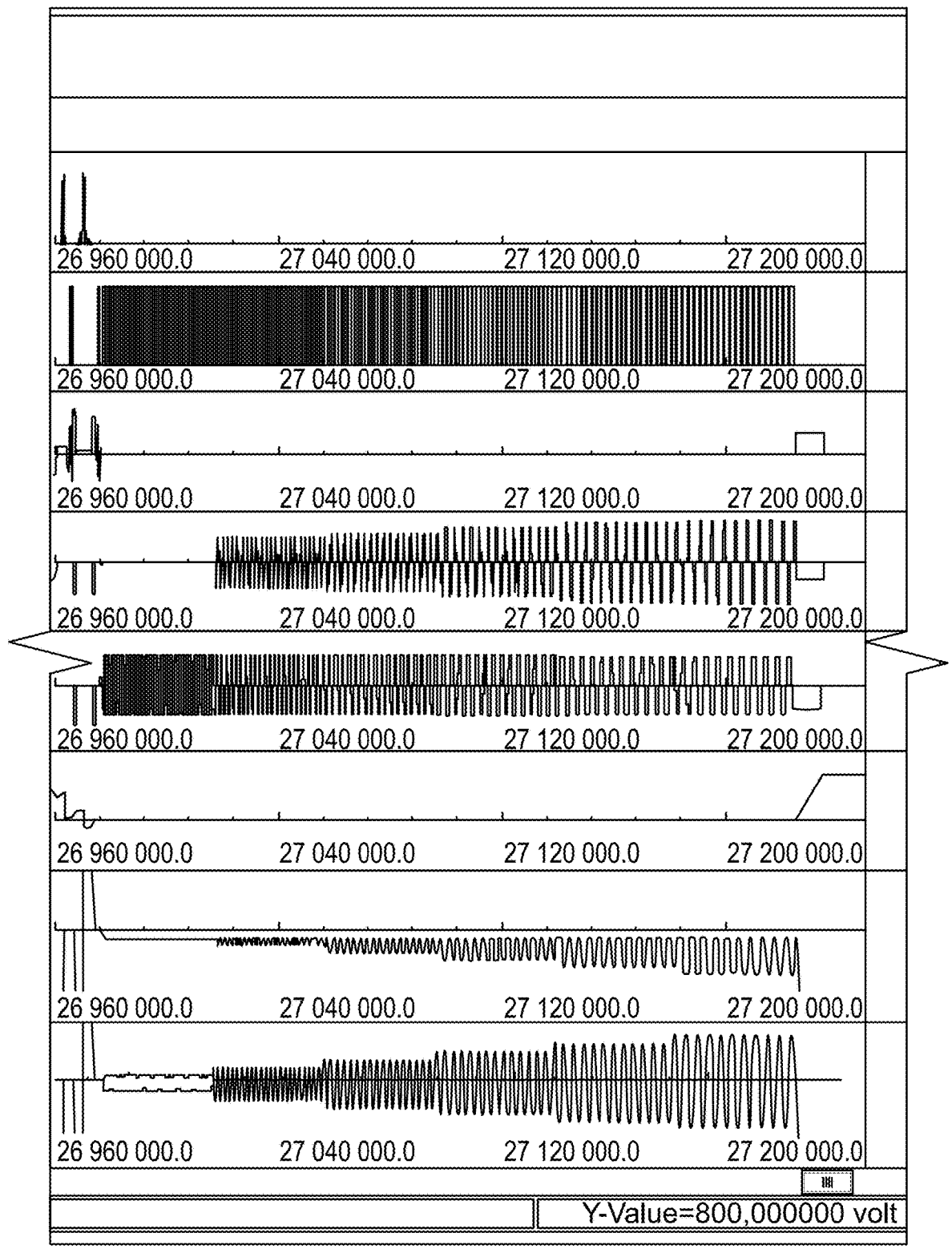
FIGS. 9A and 9B show a corresponding simulation of the central phase encoding step with maximum negative $k_y$ encoding moment (see Y Gradient and Y-Gradient moment).
Figure 9B:
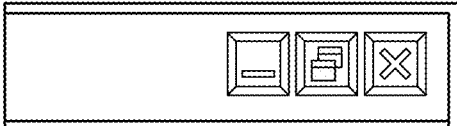
Figure 10A:
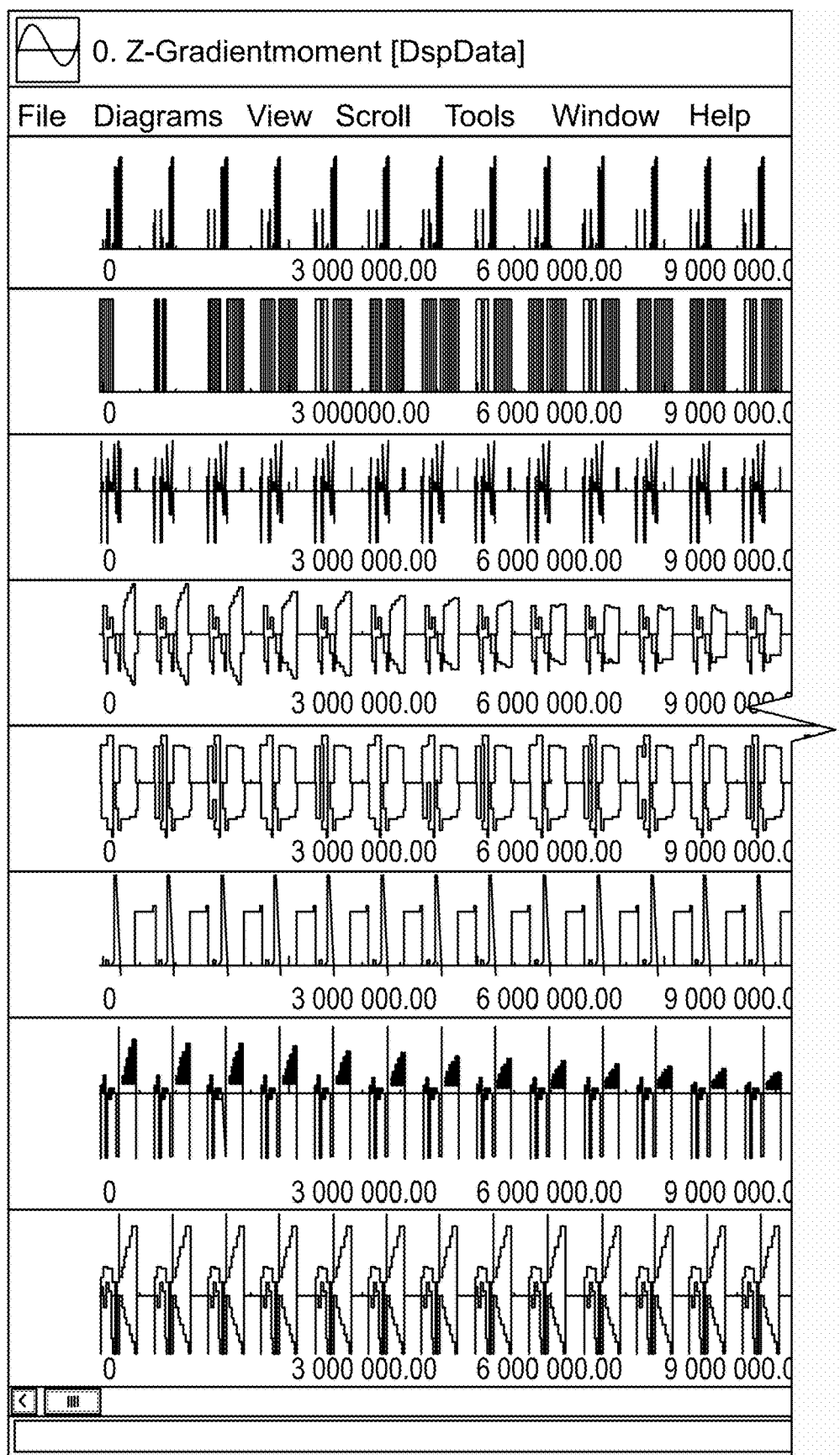
FIGS. 10A, 10B and 10C show a corresponding simulation of all phase encoding steps, including water suppression modules that precede the excitation and readout modules.
Figure 10B:
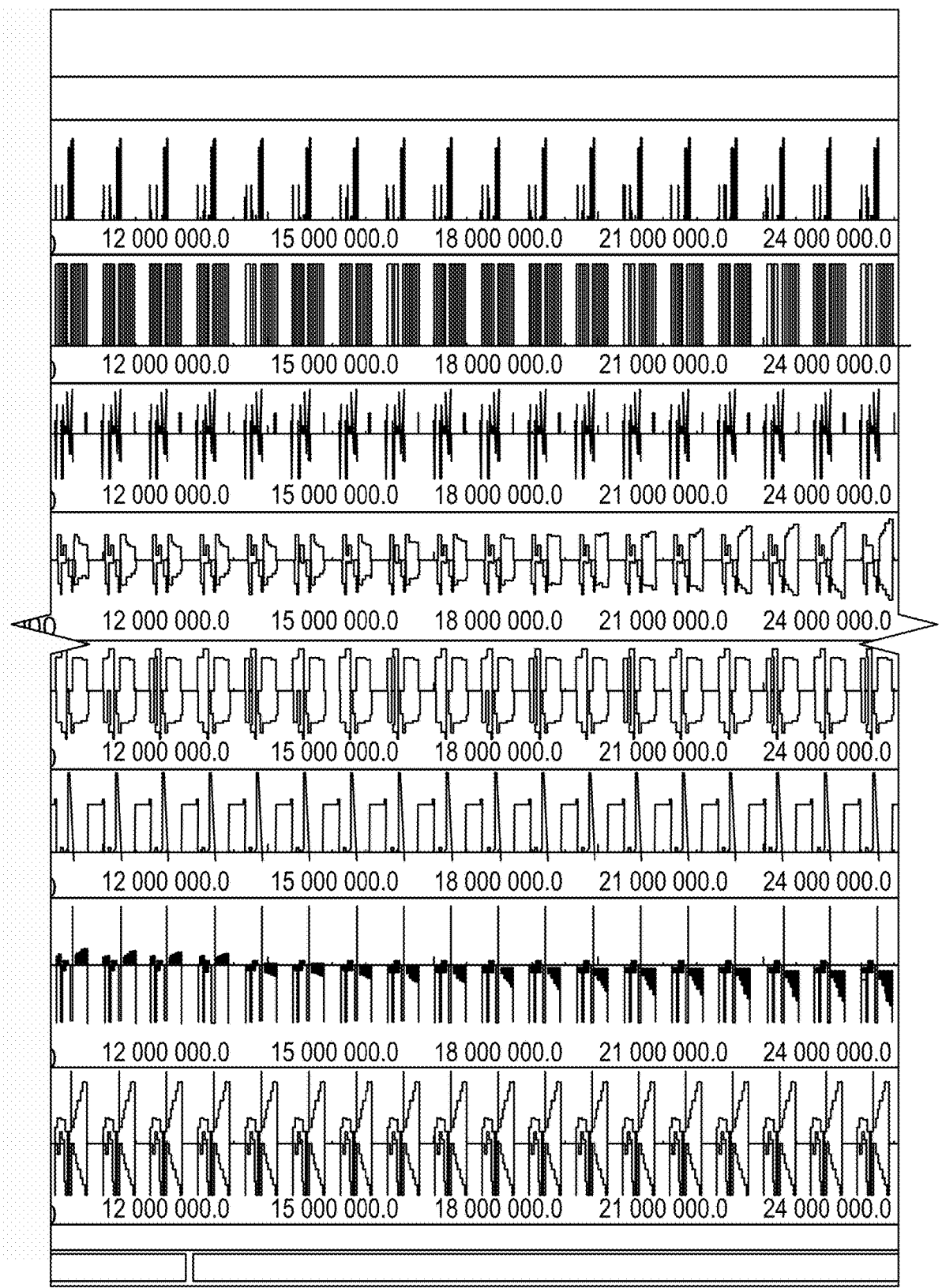
Figure 10C:
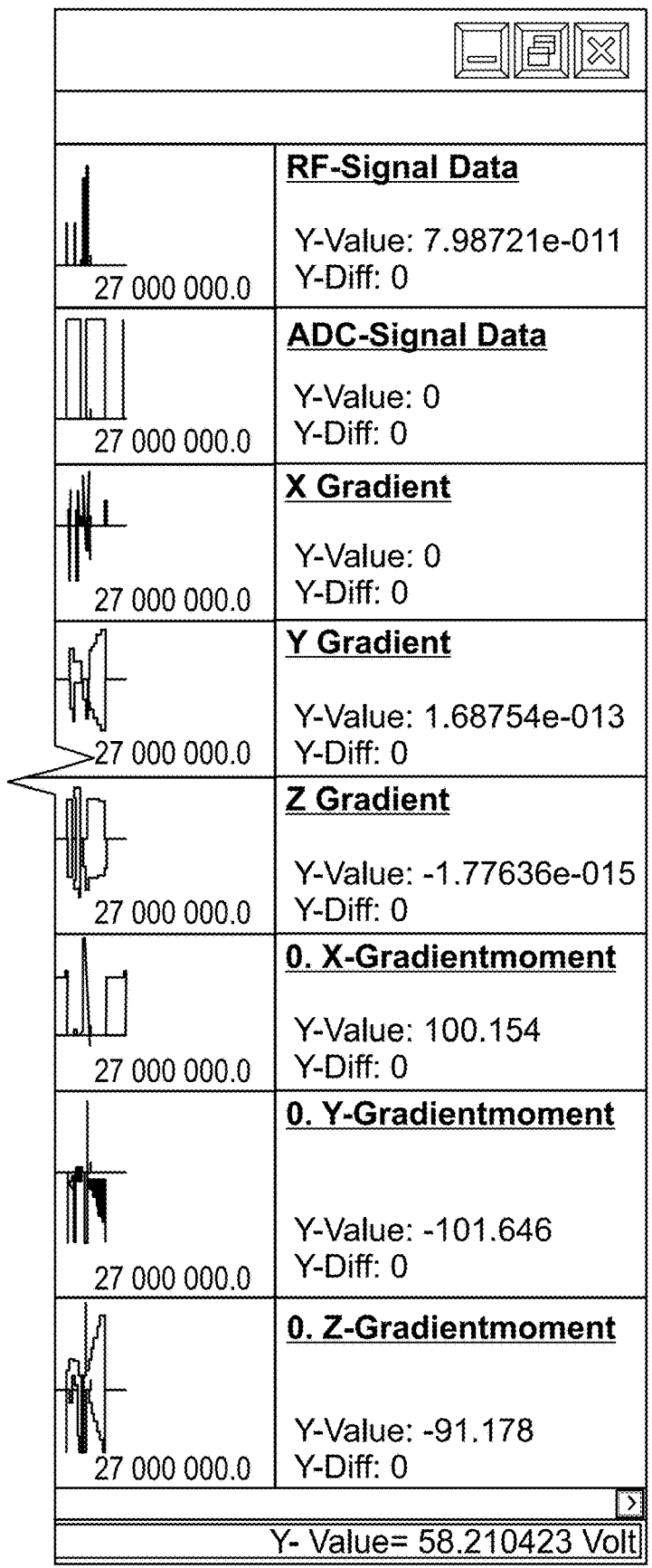
Figure 11A:
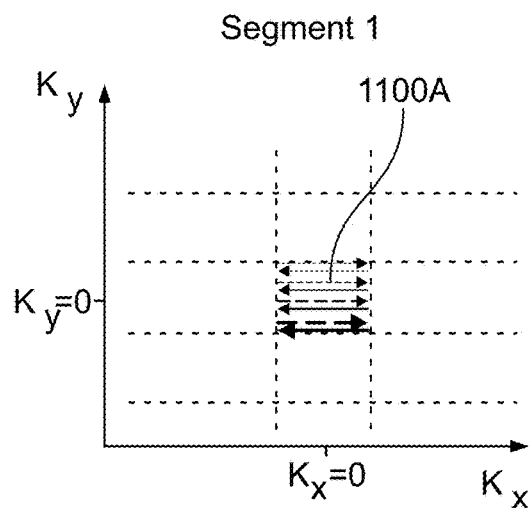
FIG. 11A shows a 2D K-space expansion of time slices in different readout segments using a combination of full k-space encoding and undersampled encoding for a full k-space encoding in segment 1.
Figure 11B:
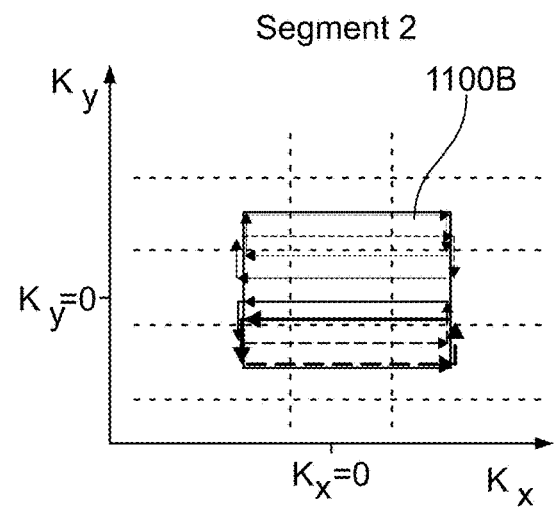
FIG. 11B shows a 2D K-space expansion of time slices in different readout segments using a combination of full k-space encoding and undersampled encoding with for a 4-fold expansion of full k-space encoding in segment 2 using 2-fold increased readout gradient moment and blipped phase encoding gradients interleaved between positive and negative readout gradients to encode outer $k_y$-space lines.
Figure 11C:
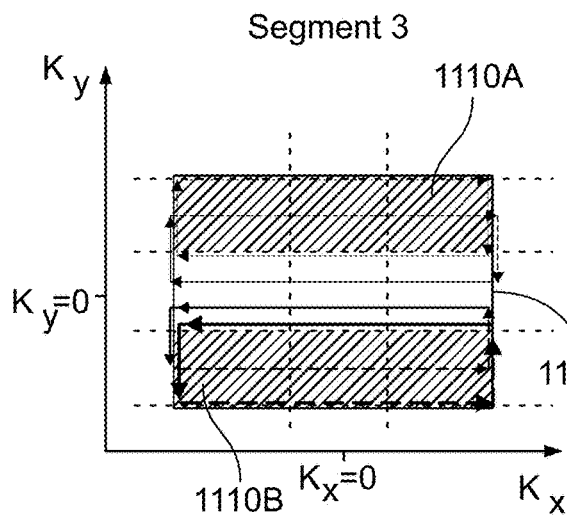
FIG. 11C shows a 2D K-space expansion of time slices in different readout segments using a combination of full k-space encoding and undersampled encoding for a 9-fold expansion of k-space encoding in segment 4 using 3-fold increased readout gradient moment and blipped phase encoding gradients interleaved between positive and negative readout gradients to encode outer $k_y$-space lines with 2-fold undersampling.
Figure 11D:
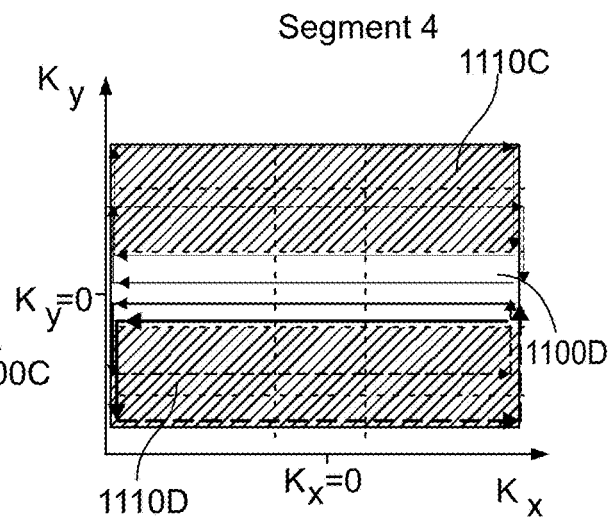
FIG. 11D shows a 2D K-space expansion of time slices in different readout segments using a combination of full k-space encoding and undersampled encoding for a 16-fold expansion of k-space encoding in segment 4 using 4-fold increased readout gradient moment and blipped phase encoding gradients interleaved between positive and negative readout gradients to encode outer $k_y$-space lines with 3-fold undersampling. Subsequent segments are acquired with correspondingly larger outer $k_y$ undersampling factors.
Figure 12A:
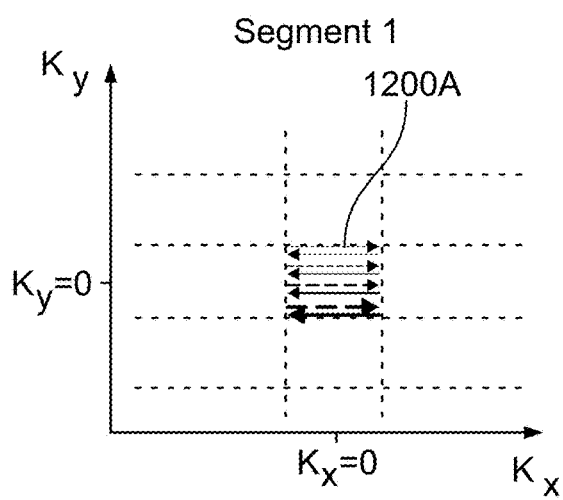
FIG. 12A shows a 2D K-space expansion of time slices in different readout segments using full k-space encoding for a full k-space encoding in segment 1.
Figure 12B:
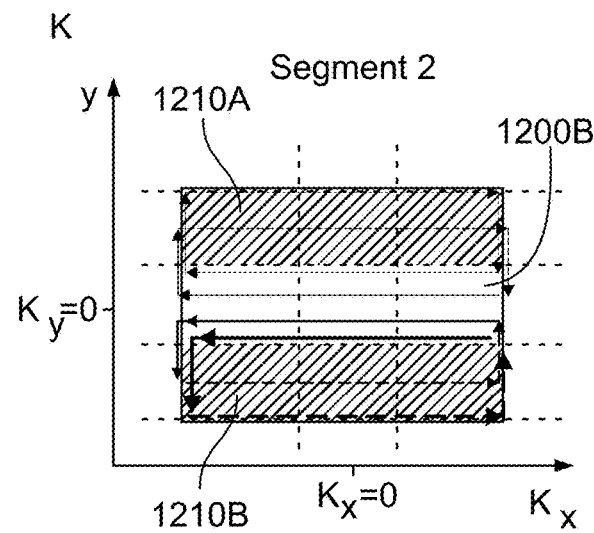
FIG. 12B shows a 2D K-space expansion of time slices in different readout segments using full k-space encoding for a 4-fold expansion of full k-space encoding in segment 2 using 2-fold increased readout gradient moment and blipped phase encoding gradients interleaved between positive and negative readout gradients to encode outer $k_y$-space lines.
Figure 12C:
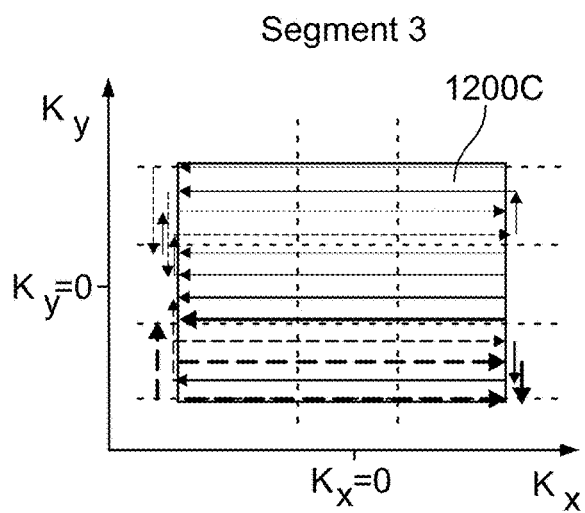
FIG. 12C shows a 2D K-space expansion of time slices in different readout segments using full k-space encoding for a 9-fold expansion of k-space encoding in segment 4 using 3-fold increased readout gradient moment and 3 blipped phase encoding gradients interleaved between positive and negative readout gradients to encode outer $k_y$-space lines.
Figure 12D:
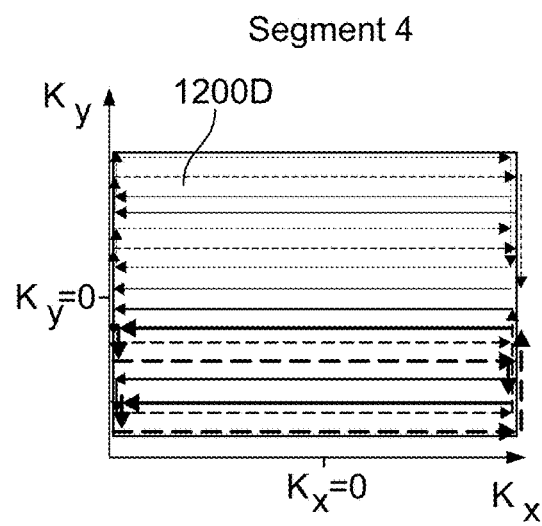
FIG. 12D shows a 2D K-space expansion of time slices in different readout segments using full k-space encoding for a 16-fold expansion of k-space encoding in segment 4 using 4-fold increased readout gradient moment and 4 blipped phase encoding gradients interleaved between positive and negative readout gradients to encode outer-space lines. Subsequent segments are acquired with a correspondingly larger number of interleaved gradient blips.

Practical Implementation of a PEPSI Pulse Sequence with Dynamic k-Space Expansion A pulse sequence was implemented on a Siemens Trio scanner (Syngo VB17A) using step-wise increases in readout gradient moments that were realized using readout gradient train segments with increasing readout gradient duration at constant ADC readout bandwidth per pixel. Interleaved alternating gradients are switched along the $k_y$ and $k_z$ axes to encode multiple $k_x$ lines in a single shot. The moments of these phase encoding gradient blips increase from segment to segment to expand $k_y$-space. The pulse sequence implementation provides flexible control of readout gradient moments, duration of readout gradient train segments, and phase encoding gradient blip moments for each readout gradient train segment and for each phase encoding step, using a combination of mathematical expressions coded in C++ inside the pulse sequence, GUI based parameter selection and a lookup table in form of an external text file to maximize flexibility. An example of the excitation and readout modules of a PEPSI pulse sequence with linear k-space expansion and 2 $k_x$ lines acquired per phase encoding step is shown in FIGS. 5A-5B. An example of the corresponding PEPSI pulse sequence with nonlinear k-space expansion is shown in FIGS. 6A-6C. FIGS. 7-10 depict simulations of different phase encoding steps of the entire PEPSI pulse sequence with embedded water reference and navigators for the case of linear k-space expansion. The corresponding k-space encoding of time slices in different readout segments is shown in FIGS. 11A-11D where full k-space encoding is shown in sections 1100A-1100D and undersampled encoding is shown in sections 1110A-1110D. Note that $k_x$ is fully sampled. Central sections of $k_y$-space are fully sampled as well, whereas peripheral sections of $k_y$ are undersampled.

FIGS. 12a-12d depict an example of expanding k-space encoding with full sampling of both $k_x$ and $k_y$, which requires interleaving of additional phase encoding blips to acquire more than 2 k-space lines in a single readout module at the expense of increasing spectral dwell time. Full k-space encoding is used along $k_y$-$k_z$ plane kx and in the center of the $k_y$-$k_z$ planes 1200A-1200D and undersampled k-space encoding 1210A and 1210B in the outer regions of the $k_y$-$k_z$ plane increases linearly from readout segment to readout segment (numbered: 1,2,3 . . . ) using increasing undersampling factors.

Figure 13:
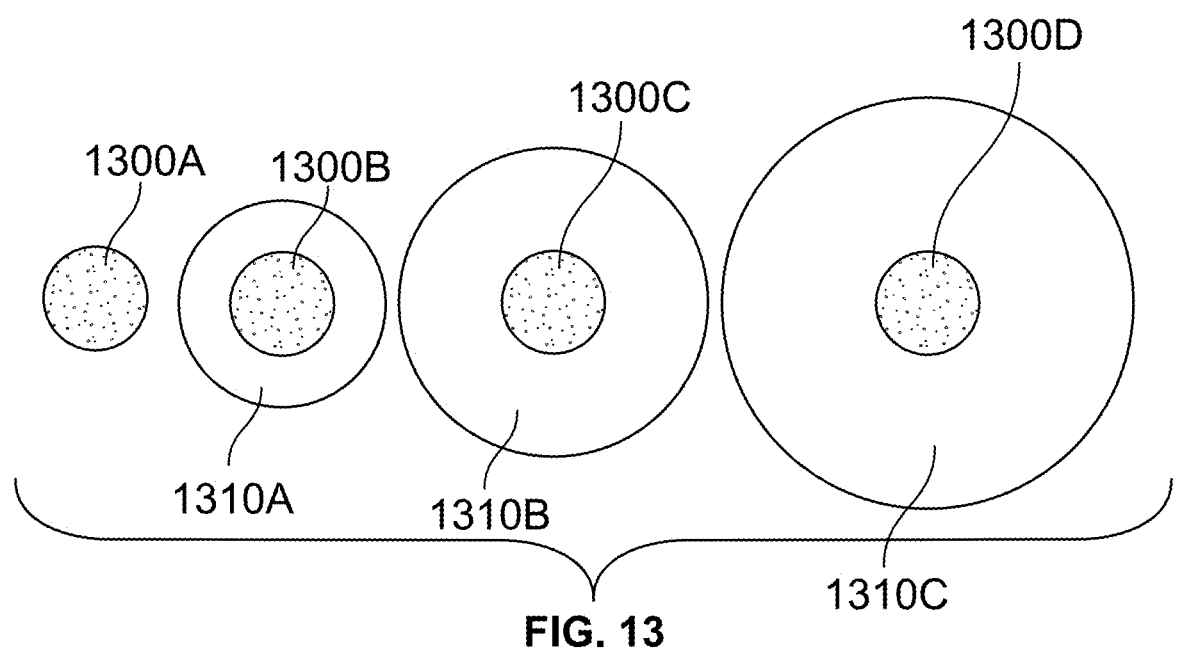
FIG. 13 shows a 3D K-space expansion of time slices in different readout segments depicted in the $k_y$-$k_z$ plane.

FIG. 13 depicts an example of expanding k-space encoding with full sampling of $k_x$ and increasing undersampling in the $k_x$-$k_y$-plane in consecutive readout segments. Full k-space encoding is used along $k_y$-$k_z$ plane kx and in the center of the $k_y$-$k_z$ plane 1300A-1300D and undersampled k-space encoding 1310A-1310C in the outer regions of the $k_y$-$k_z$ plane increases linearly from readout segment to readout segment (numbered: 1,2,3 . . . ) using increasing undersampling factors.

Figure 14A:
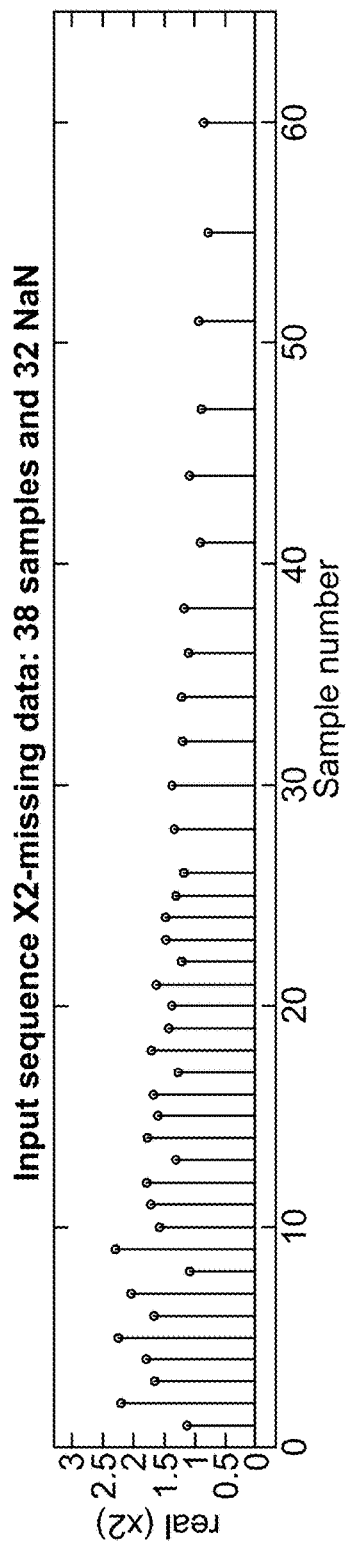
FIGS. 14A, 14B and 14C show a simulation of spectral reconstruction of undersampled data.
Figure 14B:
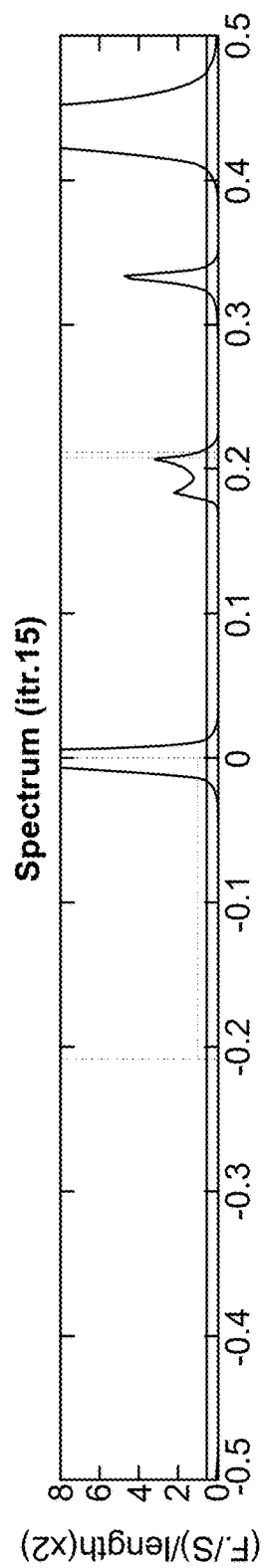
Figure 14C:
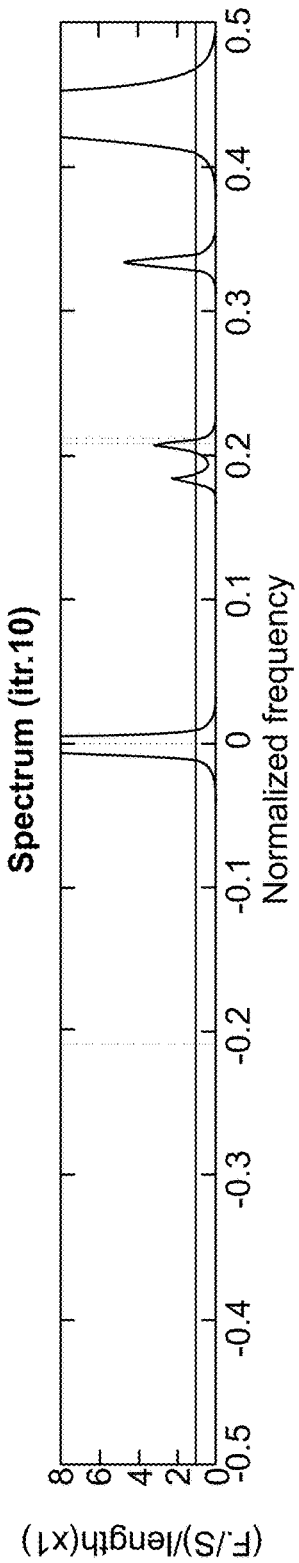

FIGS. 14A-14C demonstrate that temporally undersampled data can be reconstructed with a minor increase in spectral line width using the expanded Fourier Transform MAT LAB toolbox (https://www.mathworks.com/matlab-central/fileexchange/11020-extended-dft). FIG. 14A shows the simulated time domain data set with temporal undersampling that increases from 2-fold in the $2^{nd}$ segment to 6-fold in the 6th segment. FIG. 14B shows the reconstructed spectrum using the expanded Fourier Transform. Undersampling increases the spectral line width linewidth slightly with respect to the fully sampled data as shown in FIG. 14C but does not distort the spectral pattern. A preferred implementation of k-space expansion employs much finer discretization steps.

Figure 15A:
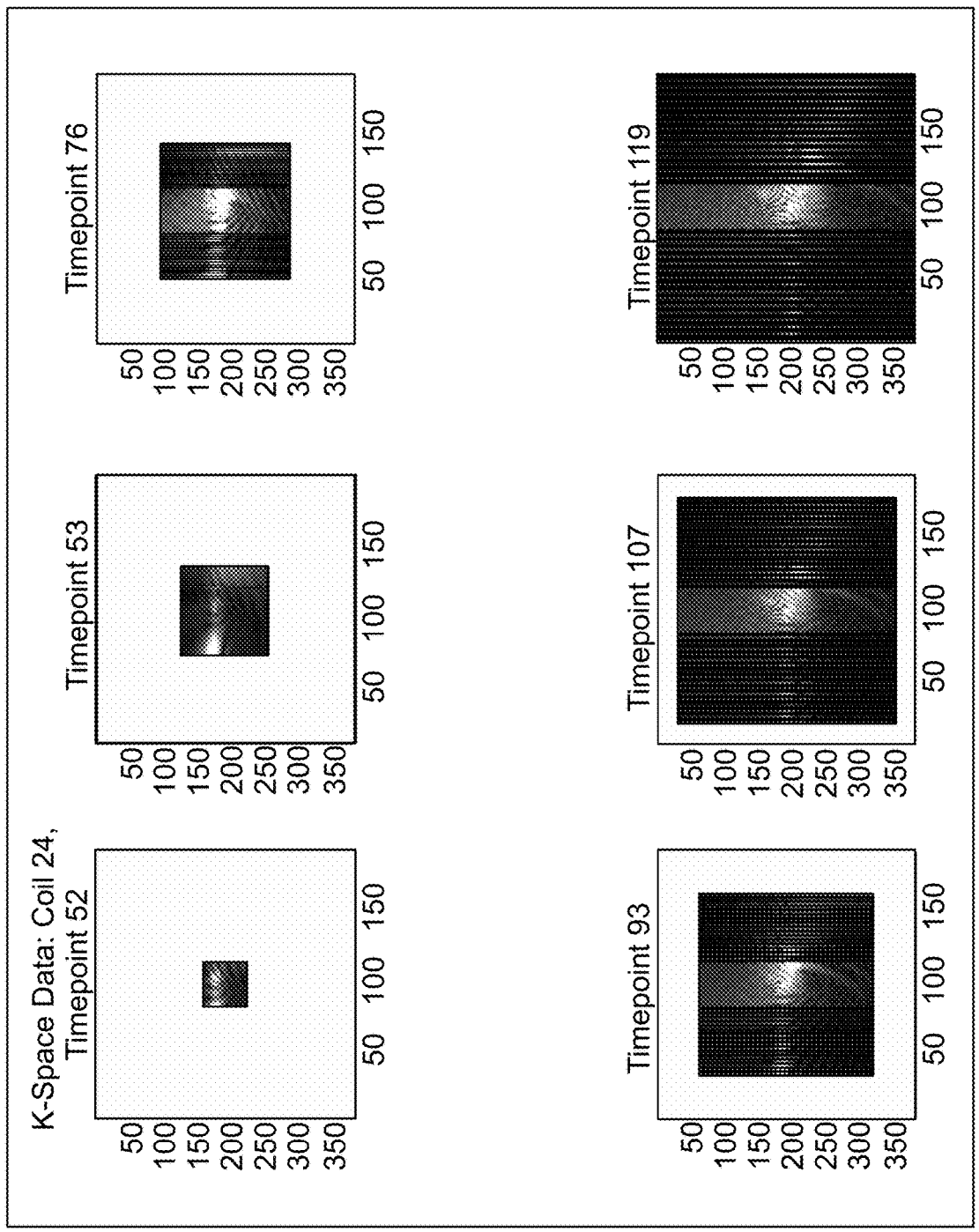
FIG. 15A shows a GRAPPA k-space reconstruction of $k_y$-undersampled raw data in a spherical phantom using OPENGRAPPA for an undersampled k-space data at selected time points at the beginning of the 6 acquired readout segments for a selected coil located in the vicinity of a susceptibility inhomogeneity due to an air bubble.
Figure 15B:
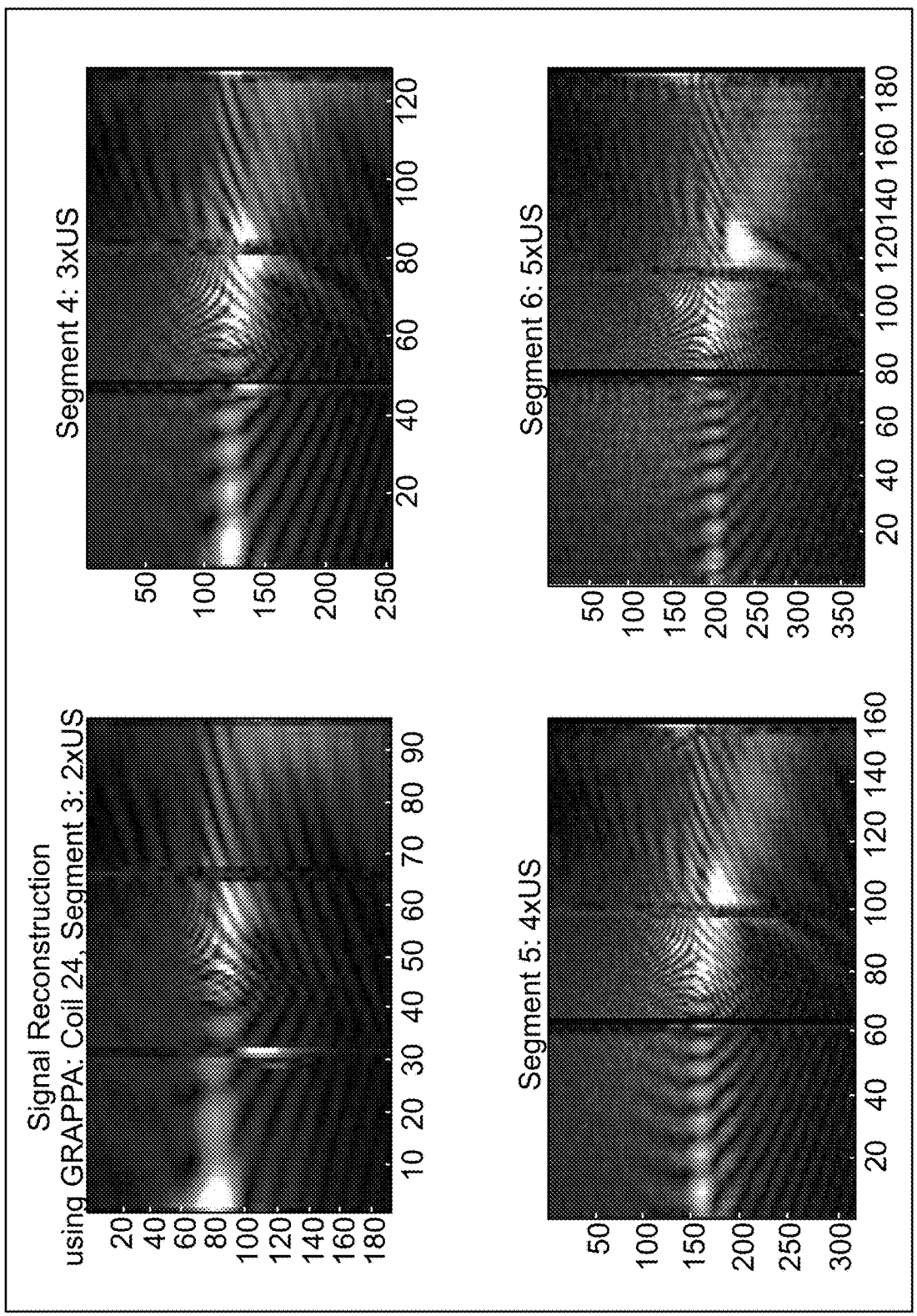
FIG. 15B shows a GRAPPA k-space reconstruction of $k_y$-undersampled raw data in a spherical phantom using OPENGRAPPA for GRAPPA reconstructed k-space data in the $k_y$-undersampled readout segments 3-6 replacing the missing data lines in the outer segments of ky space.
Figure 16A:
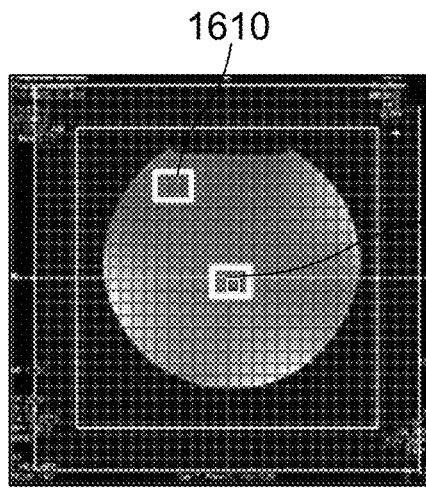
FIG. 16A shows a phantom experiment for an MRI with ROIs indicating magnetically homogeneous region and magnetically inhomogeneous region.
Figure 16B:
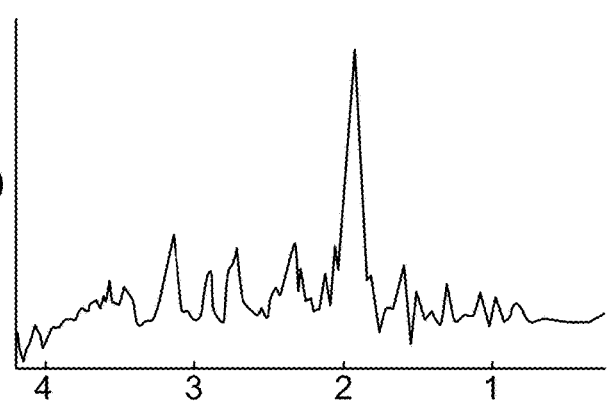
FIG. 16B shows a phantom experiment for an undersampled spectrum with k-space expansion from the central magnetically uniform region reconstructed using the expanded Fourier transform.
Figure 16C:
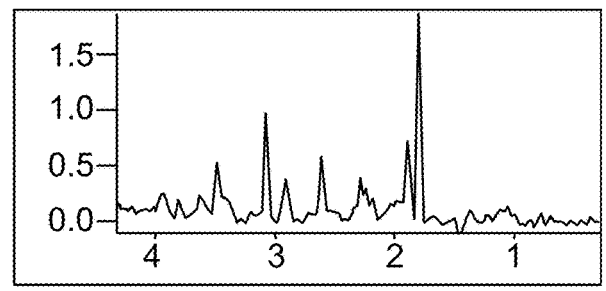
FIG. 16C shows a phantom experiment for a corresponding spectrum reconstructed online from fully sampled data without k-space expansion using conventional PEPSI.
Figure 16D:
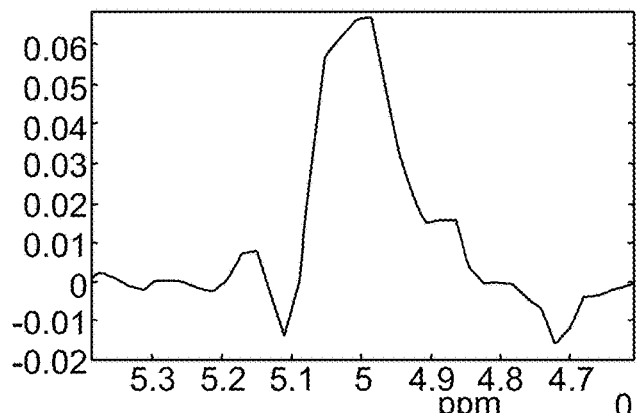
FIG. 16D shows a phantom experiment for a spectrum without k-space expansion from the magnetically inhomogeneous region close to the air bubble shows a broad water peak.
Figure 16E:
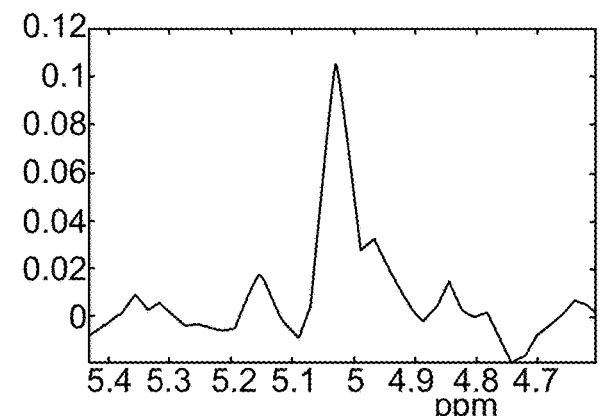
FIG. 16E shows a phantom experiment for a corresponding water spectrum with k-space expansion shows a narrower spectral line width.
Figure 17A:
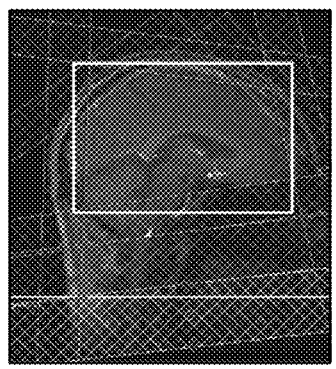
FIG. 17A shows a 2D PEPSI data acquired in a healthy control with 2D K-space expansion for an anatomical localizer with sagittal PEPSI slice prescription and outer volume suppression slices.
Figure 17B:
FIG. 17B shows a 2D PEPSI data acquired in a healthy control with 2D K-space expansion for a first time slice of water suppressed data maps, which maps residual water with a strong signal in inferior frontal cortex that corresponds to a brain region with strong magnetic field inhomogeneity and local frequency shifts in which the water suppression efficiency was reduced.
Figure 17C:
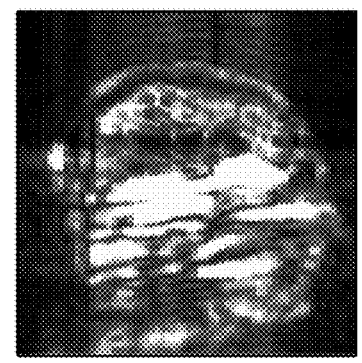
FIG. 17C shows a 2D PEPSI data acquired in a healthy control with 2D K-space expansion for a threshold ratio map of the residual signal in the first w.r.t. the last time slice for the acquisition without k-space expansion that shows a particularly strong signal loss in inferior brain regions due to magnetic field inhomogeneity (threshold: 40).
Figure 17D:
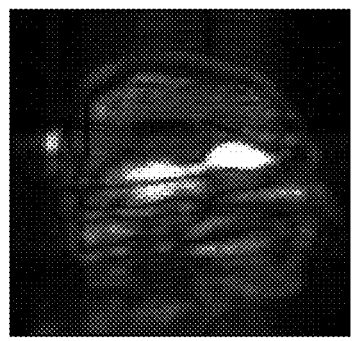
FIG. 17D shows a 2D PEPSI data acquired in a healthy control with 2D K-space expansion for a corresponding ratio for acquisition with 6×6-fold k-space expansion shows considerably reduced signal loss in most brain regions except centrum semiovale.
Figure 17E:
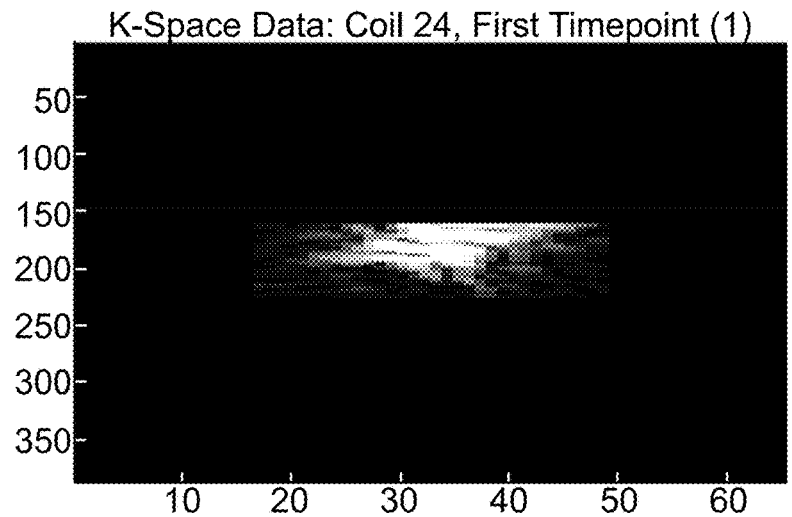
FIG. 17E shows a 2D PEPSI data acquired in a healthy control with 2D K-space expansion for K-space raw data in the first time slice of the acquisition with 6×6-fold k-space expansion for coil 24 in, which is adjacent to the frontal cortex.
Figure 17F:
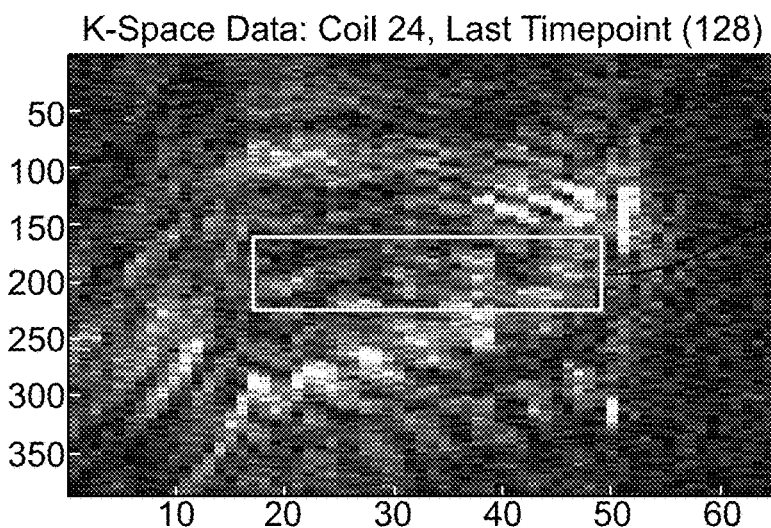
FIG. 17F shows a 2D PEPSI data acquired in a healthy control with 2D K-space expansion for corresponding k-space raw data in the last time slice, which illustrates the considerable dispersion of signals along $k_x$ and $k_y$.

Data were acquired in a spherical phantom containing metabolites and in a healthy control using a Siemens Trio 3 Tesla MRI scanner equipped with 32-channel head array RF coil. Water reference and water suppressed data were acquired in a sagittal or axial slice using TR/TE=2200/15 ms, 32×32 spatial matrix, 8×8×20 mm³ nominal voxel size and 1:24 min scan time. Water reference data were acquired with 150 readout gradients. Water-suppressed data were acquired with 256 readout gradients. The readout was along the z-axis. Six equidistant readout segments with linearly increasing k-space expansion (1×, 2×, 3×, 4×, 5× and 6×, along both $k_x$ and $k_y$) were used. Undersampling of $k_y$-encoding increased from 2-fold in the $3^{rd}$ segment to 5-fold in the 6th segment. Accordingly, the acquired spatial data matrix in the 6th readout segment was 392×64 complex data points (readout×phase encoding) and time slice undersampling increased from 2-fold in the $2^{nd}$ segment to 6-fold in the $6^{th}$ segment. Data were reconstructed offline using zero filling of the readout direction to obtain a consistent matrix size of 392×64 data points (readout×phase encoding) for all time slices. FIGS. 15A-15B show k-space raw data acquired in the phantom using increasing $k_y$-undersampling in readout segments 3-6 and k-space reconstructed data using the OPENGRAPPA. FIGS. 16A-16E display localized spectra in magnetically uniform and inhomogeneous regions of the phantom, reconstructed from undersampled data using the expanded Fourier Transform, that illustrate the improved spectral linewidth obtained with k-space expansion. FIG. 16A shows magnetically homogeneous region 1600 and magnetically inhomogeneous region 1610. FIGS. 17A-17F summarize the in vivo data and shows that the signal decrease in most brain regions is strongly reduced with k-space expansion. The signal gain at the last time slice, which corresponds to an acquisition delay of 500 ms, ranges from 3-fold in occipital and parietal cortex to 4-fold in the frontal cortex. FIGS. 17E and 17F show the signal distribution in k-space in the first and the last slice for a receiver coil located adjacent to the frontal cortex, which illustrates the increase in signal dispersion in k-space with measurement time. Box 1700 in FIG. 17F corresponds to the conventional k-space coverage without k-space expansion.

The k-space expansion method can be expanded to 3D spatial encoding: The preferred implementation of k-space undersampling for a volumetric PEPSI acquisition employs radial undersampling in the $k_y$-$k_z$ plane that increases with increasing radius.

While the foregoing description applies to MR spectroscopic imaging, the k-space expansion methodology also applies to gradient echo MR imaging and functional MR imaging, reducing magnetic field inhomogeneity related signal losses and sensitivity to movement-related signal changes in regions with magnetic field inhomogeneity.

While the foregoing written description enables one of ordinary skill to make and use what is considered presently to be the best mode thereof, those of ordinary skill will understand and appreciate the existence of variations, combinations, and equivalents of the specific embodiment, method, and examples herein. The disclosure should therefore not be limited by the above-described embodiments, methods, and examples, but by all embodiments and methods within the scope and spirit of the disclosure.

What is claimed is:

1. A method for the compensation of magnetic field inhomogeneity in magnetic resonance spectroscopic imaging comprising the steps of using dynamic k-space expansion in combination with parallel imaging; said k-space is expanded with increasing spectral encoding time t, resulting in spectral line narrowing in proportion to the expansion of k-space; and minimizing gradient switching by tailoring the expansion and density of k-t-space sampling to the dispersion and density of signal trajectories in k-t-space.

2. The system and method of claim 1 wherein said expansion of the k-space with spectral encoding time includes interleaving progressively larger spatial encoding gradient moments.

3. The method of claim 1 wherein expanding the k-space is accomplished by extending high speed image encoding modules, including echo-planar and spiral encoding modules.

4. The method of claim 1 wherein said k-space is undersampled regularly and compressed sensing is used to reconstruct the missing data.

5. The method of claim 1 wherein said k-space is under sampled randomly and compressed sensing is used to reconstruct the missing data.

6. The method of claim 1 wherein said expansion of k-t-space is linear and employs readout gradient moment with stepwise increases ($2G_l \delta t$) every second gradient using a constant gradient duration δ, up to the limits of the gradient performance.

7. The method of claim 1 wherein single-shot phase encoding using gradient blips with linearly increasing gradient moment $G_l$*t are selectively interleaved into the readout, with a corresponding increase of the effective spectral dwell time.

8. The method of claim 7 wherein said interleaving starts at the edges of the original $k_y$-$k_z$-space and progressively inserts single-shot phase encoding into more central $k_y$-$k_z$-space encodings as time t increases.

9. The method of claim 1 wherein the k-space dimensions are tailored to the orientation and amplitude distribution of local Gradients $G_l$ based on $B_0$ gradient maps.

10. The method of claim 1 further including the step of compensating local gradients in a selected brain region and simultaneously acquiring signals from the rest of the brain without compensation.

11. A method for the compensation of magnetic field inhomogeneity in magnetic resonance spectroscopic imaging comprising the steps of using dynamic k-space expansion in combination with parallel imaging; and said k-space is expanded with increasing spectral encoding time t, resulting in spectral line narrowing in proportion to the expansion of k-space; and wherein said k-space is undersampled regularly and partial parallel imaging is used to reconstruct the missing data.

12. A method for the compensation of magnetic field inhomogeneity in magnetic resonance spectroscopic imaging comprising the steps of using dynamic k-space expansion in combination with parallel imaging; and said k-space is expanded with increasing spectral encoding time t, resulting in spectral line narrowing in proportion to the expansion of k-space; and wherein said k-space is under sampled randomly and compressed sensing is used to reconstruct the missing data.

* * * * *